(12) United States Patent
Lee et al.

(10) Patent No.: US 11,262,349 B2
(45) Date of Patent: Mar. 1, 2022

(54) MULTIPLEXED IMMUNE CELL ASSAYS ON A MICROPILLAR/MICROWELL CHIP PLATFORM

(71) Applicant: Cleveland State University, Cleveland, OH (US)

(72) Inventors: Moo-Yeal Lee, Pepper Pike, OH (US); Xue-Long Sun, Solon, OH (US)

(73) Assignee: Cleveland State University, Cleveland, OH (US)

( * ) Notice: Subject to any disclaimer, the term of this patent is extended or adjusted under 35 U.S.C. 154(b) by 110 days.

(21) Appl. No.: 16/157,727

(22) Filed: Oct. 11, 2018

(65) Prior Publication Data

US 2019/0107532 A1 Apr. 11, 2019

Related U.S. Application Data

(60) Provisional application No. 62/570,965, filed on Oct. 11, 2017.

(51) Int. Cl.
*G01N 33/50* (2006.01)
*G01N 33/543* (2006.01)

(52) U.S. Cl.
CPC ..... *G01N 33/5047* (2013.01); *G01N 33/5023* (2013.01); *G01N 33/54386* (2013.01)

(58) Field of Classification Search
CPC ........... G01N 33/5023; G01N 33/5047; G01N 33/54386
See application file for complete search history.

(56) References Cited

U.S. PATENT DOCUMENTS 4,871,647 A 10/1989 Komamura et al.
6,022,700 A * 2/2000 Monks ................ B01J 19/0046
356/244

(Continued)

FOREIGN PATENT DOCUMENTS

CA 2398271 A1 8/2001
CN 101218028 A 7/2008

(Continued)

OTHER PUBLICATIONS

Datar et al. Biocompatible hydrogels for microarray cell printing and encapsulation. Biosensors 2015, vol. 5, pp. 647-663. (Year: 2015).*

(Continued)

*Primary Examiner* — Shafiqul Haq
(74) *Attorney, Agent, or Firm* — Calfee, Halter & Griswold LLP

(57) ABSTRACT

A multiplexed method of monitoring immune-cell responses to different ligands using a micropillar/microwell plate platform is disclosed. The method may include dispensing immune cells onto at least one micropillar chip and inserting the at least one micropillar into at least one microwell on a microwell chip, in which the at least one microwell contains at least one test compound. The method may also include immobilizing antibodies onto at least one micropillar on a micropillar chip and inserting the at least one micropillar into at least one microwell on a microwell chip, in which the at least one microwell contains a test compound. The method may also include treating the micropillar chip with at least one reactive polymer.

11 Claims, 18 Drawing Sheets

US 11,262,349 B2
Page 2

(56) References Cited

U.S. PATENT DOCUMENTS

| | | | |
|---|---|---|---|
| 7,148,058 B2* | 12/2006 | Charych | B01J 19/0046 |
| | | | 435/287.8 |
| 7,332,328 B2 | 2/2008 | Webb et al. | |
| 8,778,849 B2 | 7/2014 | Bowen et al. | |
| 9,097,702 B2 | 8/2015 | Fischbach | |
| 9,133,429 B2 | 9/2015 | Higuera et al. | |
| 9,481,868 B2 | 11/2016 | Nguyen et al. | |
| 9,758,533 B2* | 9/2017 | Tuttle | C07K 16/2863 |
| 10,605,708 B2 | 3/2020 | Shao | |
| 2003/0124029 A1 | 7/2003 | Webb | |
| 2004/0197236 A1 | 10/2004 | Vanmaele | |
| 2008/0103059 A1* | 5/2008 | Webb | B01L 3/5025 |
| | | | 506/9 |
| 2009/0263849 A1 | 10/2009 | Sun et al. | |
| 2011/0152128 A1 | 6/2011 | Hermann et al. | |
| 2011/0190162 A1 | 8/2011 | Lee et al. | |
| 2011/0212501 A1 | 9/2011 | Yoo | |
| 2011/0259742 A1 | 10/2011 | Li | |
| 2012/0088693 A1 | 4/2012 | Lee et al. | |
| 2012/0135890 A1 | 5/2012 | Shin | |
| 2012/0165224 A1 | 6/2012 | Song et al. | |
| 2012/0183636 A1 | 7/2012 | Kim et al. | |
| 2013/0081483 A1 | 4/2013 | Jeong et al. | |
| 2014/0045256 A1 | 2/2014 | Lee et al. | |
| 2014/0154722 A1 | 6/2014 | Yeal et al. | |
| 2014/0170671 A1 | 6/2014 | McGarr | |
| 2014/0227145 A1 | 8/2014 | Kim et al. | |
| 2014/0273053 A1 | 9/2014 | Lee et al. | |
| 2014/0287960 A1 | 9/2014 | Shepard et al. | |
| 2015/0005180 A9 | 1/2015 | Ishihara et al. | |
| 2015/0086445 A1 | 3/2015 | Lee et al. | |
| 2015/0101070 A1 | 4/2015 | Nam et al. | |
| 2015/0282885 A1 | 10/2015 | King et al. | |
| 2016/0074558 A1 | 3/2016 | Murphy et al. | |
| 2016/0122723 A1 | 5/2016 | Retting et al. | |
| 2016/0348049 A1 | 12/2016 | Baba | |
| 2017/0141503 A1 | 5/2017 | Eckel et al. | |
| 2017/0198275 A1 | 7/2017 | Lee | |

FOREIGN PATENT DOCUMENTS

| | | | |
|---|---|---|---|
| CN | 102246037 A | 11/2011 | |
| CN | 102836751 A | 12/2012 | |
| CN | 103930066 | 7/2014 | |
| CN | 104717987 | 6/2015 | |
| CN | 105381903 A | 3/2016 | |
| CN | 105521841 | 4/2016 | |
| CN | 105964313 A | 9/2016 | |
| EP | 1310794 | 5/2003 | |
| EP | 3040723 | 7/2016 | |
| KR | 20140072883 | 6/2014 | |
| KR | 201600336619 | 4/2016 | |
| WO | WO-9309872 A1 * | 5/1993 | B01L 3/5085 |
| WO | 2001007891 | 2/2001 | |
| WO | 2005098432 A1 | 10/2005 | |
| WO | 2006078814 A2 | 7/2006 | |
| WO | 2007053561 | 5/2007 | |
| WO | 2012034022 | 3/2012 | |
| WO | 2012125906 | 9/2012 | |
| WO | 2012158875 | 11/2012 | |
| WO | 2013041901 | 3/2013 | |
| WO | 2015121302 A1 | 8/2015 | |
| WO | 2017123722 | 7/2017 | |

OTHER PUBLICATIONS

European Partial Search Report and Provisional Opinion for EP Appln No. 17871475.4 dated May 29, 2020.
Extended European Search Report for EP Appln No. 17871475.4 dated Sep. 2, 2020.
International Search Report and Written Opinion from PCT/US17/062266 dated Mar. 7, 2018.
International Search Report and Written Opinion from PCT/US17/013144 dated Mar. 30, 2017.
Lee, D.W et al., "Automatic 3D Cell Analysis in High-Throughput Microarray Using Micropillar and Microwell Chips," Journal of Biomolecular Screening, 2015, 1178-1184, Society for Laboratory Automation and Screening.
Kwon, S.J. et al., "High-throughput and combinatorial gene expression on a chip for metabolism-induced toxicology screening," Nature Communications, May 6, 2014, 5:3739, DOI 10.1038/ncomms4739, 2014 Macmillan Publ. Ltd.
Lee, D.W. et al., "High-Throughput Screening (HTS) of Anticancer Drug Efficacy on a Micropillar/Microwell Chip Platform," Analytical Chemistry, 2014, 86(1), 535-542, ACS Publications.
Lee, D.W. et al., "Application of the DataChip/MetaChip technology for the evaluation of ajoene toxicity in vitro," Archives of Toxicology, 88(2), 283-290, Jul. 28, 2013 Springer.
Lee, D.W. et al., "Plastic pillar inserts for three-dimensional (3D) cell cultures in 96-well plates," Sensors and Actuators B, 177(1), 2013, 78-85, Elsevier B.V.
Zhang, H.Y. et al., "High-Throughput Transfection of Interfering RNA into a 3D Cell-Culture Chip," Small, 8(13), 2091-2098, Jul. 2012.
Fernandes, T.G. et al., "Three-Dimensional Cell Culture Microarray for High-Throughput Studies of Stem Cell Fate," Biotechnology and Bioengineering, vol. 106, No. 1, 106-118, May 1, 2010.
Park, T.J., et al., "Signal Amplification of Target Protein on Heparin Glycan Microarray," Analytical Biochemistry, 383, 116-121, Dec. 1, 2008.
Fernandes, T.G. et al., "On-Chip, Cell-Based Microarray Immunofluorescence Assay for High-Throughput Analysis of Target Proteins," Analytical Chemistry, 80, 6633-6639, Sep. 1, 2008.
Lee, M.Y. et al., "Three-dimensional cellular microarray for high-throughput toxicology assays," Proc. of the Nat'l. Academy of Sciences (PNAS), 105(1), 59-63, Jan. 8, 2008.
Kwon, S.J. et al., "High-Throughput, Microarray-Based Synthesis of Natural Product Analogues via in vitro Metabolic Pathway Construction," ACS Chemical Biology, 2(6), 419-425, May 25, 2007.
Lee, M.Y. et al., "Human P450 Microarrays for In Vitro Toxicity Analysis: Toward Complete Automation of Human Toxicology Screening," Journal of the Assn, for Lab. Automation, 11(6), 374-380, Dec. 2006.
Lee, M.Y. et al., "Metabolizing enzyme toxicology assay chip (MetaChip) for high-throughput microscale toxicity analyses," Proc. of the Nat'l. Academy of Sciences (PNAS), 102(4), 983-987, Jan. 25, 2005.
Lee, D.W. et al., "High-Throughput, Miniaturized Clonogenic Analysis of a Limiting Dilution Assay on a Micropillar/Microwell Chip with Brain Tumor Cells," Small, 10(24), 5098-5105, 2014 Wiley-VCH Verlag GmbH & Go. KGaA, Weinheim.
Tang, J. et al., Straightforward Synthesis of N-Glycan Polymers from Free Glycans via Cyanoxyl Free Radical-Mediated Polymerization, ACS MacroLetters 6, 107-111 (2017).
Lee, D.W. et al., "Estimation of bisphenol A—Human toxicity by 3D cell culture arrays, high throughput alternatives to animal tests," Toxicology Letters, 259, 87-94 (2016).
Kang, J.H. et al., "Mini-pillar array for hydrodel-supported 3D cell culture and and high-content histologic analysis of human tumor spheroids," Lab on a Chip, DOI: 10.1039/c6lc00526h (2016).
Wang, D. et al., "Globally profiling sialylation status of macrophages upon statin treatment," Glycobiology, 25, 1007-1015 (2015).
Mills, C.D. et al., "Macrophages at the fork in the road to health or disease," Front. Immunol. 6-59 (2015).
Sica, A. Mantovani, "Macrophage plasticity and polarization: in vivo veritas," J. Clin. Invest. 122(3), 787-795 (2012).
Liu, G. et al., "Modulation of macrophage activation and programming in immunity," J Cell Physiol. 228(3) 502-812 (2013).
Hangai, S. et al., "Innate immune receptors in the regulation of tumor immunity," In: Zitvogel L., Kroemer G. (eds) Oncoimmunology. Springer. Cham 407-427 (2018).
O'Reilly, M.K. et al., "Siglecs as targets for therapy in immune-cell-mediated disease," Trends Pharmacol. Sci. 30(5) 240-248 (2009).

(56) References Cited

OTHER PUBLICATIONS

Crocker, P.R. et al., "Siglecs and their roles in the immune system," Nat. Rev. Immunol. 7(4) 255-66 (2007).
O'Neill, A.S. et al., "Sialoadhesin—macrophage-restricted marker of immunoregulation and inflammation," Immunology 138(3) 198-207(2013).
Miyazaki, K. et al., "Colonic epithelial cells express specific ligands for mucosal macrophage immunosuppressive receptors Siglec-7 and -9," J. Immunol. 188(9) 4690-4700 (2012).
Bull, C. et al., "Sialic acid mimetrics to target the sialic acid-Siglec axis," Trends Biochem Sci. 41(6) 519-531 (2016).
Lundahl, M.L.E. et al., "Therapeutic potential of carbohydrates as regulators of macrophage activation," Biochem Pharmacol. 146 23-41 (2017).
O'Reilly, M.K., "Multivalent ligands for Siglecs," Methods Enzymol. 478 343-363 (2010).
Mannem, M. et al., "Polyvalent iteractions in biological systems: implications for design and use of multivalent ligands and inhibitors," Angew. Chem. 37(20) 2754-2794 (1998).
Lin, K. et al., "Carbohydrate-based polymers for immune modulation," ACS Macro Letters 3(7) 652-657 (2014).
Misharin, A.V. et al., "Flow cytometric analysis of macrophages and dendritic cell subsets in the mouse lung," Am. J. Respir. Cell Mol. Biol. 49(4) 503-510 (2013).
Stenken, J.A. et al., "Bioanalytical chemistry of cytokines—a review," Analytica Chimica Acta 853 95-115 (2015).
Yu, K.N. et al., "High-throughput metabolism-induced toxicity assays demonstrated on a 384-pillar plate," Archives of Toxicology 92 2501-2516 (2018).
Saxena, R.K. et al., "Evidence for lipopolysaccharide induced differentiation of Raw264.7 murine macrophage cell line into dendritic like cells," J. Biosci. (Bangalore) 28(1) 129-134 (2003).
Wu, G.J. et al., "Chitooligosaccharides from the shrimp chitosan hydrolysate induces differentiation of murine RAW264.7 macrophages into dendritic-like cells," J. Fund. Foods 12 70-79 (2015).
Iwamoto, M. et al., "Structure-activity relationship of alginate oligosaccarides in the induction of cytokine production from RAS264.7 cells," FEBS. Lett. 579 4423-4429 (2005).
Iwamoto, Y. et al., "Enzymatically depolymerized alginate oligomers that cause cytotoxic cytokine production in human mononuclear cells," Biosci. Biotechnol. Biochem. 67 258-263 (2003).
Murray, M.Y. et al., "Macrophage migration and invasion is regulated by MMP10 expression," PLoS One. 8(5) e63555 (2013).
Dwyer, A.R. et al., "A three-dimensional co-culture system to investigate macrophage-dependent tumor cell invasion," J. Biol. Methods 3(3) e49 (2016).
Lee, M.Y. et al., "Three-dimensional cellular microarray for microscale toxicology assay," Proceedings of the Natl. Acad. of Sci. of the USA (PNAS), 105(1) 59-63 (2008).
Joshi, P. et al., "High-content imaging assays on a miniaturized 3D cell culture platform," Tox. In Vitro, 50, 147-159 (2018).
Roth, A.D. et al., "Polymer coating on a micropillar chip for robust attachment of PuraMatrix peptide hydrogel for 3D hepatic cell culture," Mat Sci. and Eng C, 90, 634-644 (2018).
May, A.P. et al., "Crystal structure of the N-terminal domain of dialoadhesin in complex with 3' sialyllactose at 1.85 A resolution," Mol. Cell 1(5), 719-728 (1998).
Kawasaki T. et al., "Isolation and characterization of a receptor lectin specific for galactose/N-acetylgalactosamine from macrophages," Carbohydr. Res. 151, 197-206 (1986).
Lepenies, B. et al., "Targeting C-type lectin receptors with multivalent carbohydrate ligands," Adv. Drug Deliv. Rev. 65(9) 1271-1281 (2013).
Duque, G.A. et al., "Macrophage cytokines: involvement in immunity and infectious diseases," Front Immunol. 5, 491 (2014).
Sharman, J. et al., "An open-label phase 2 trial of entospletinib (GS-9973), a selective spleen tyrosine kinase inhibitor, in chronic lymphocytic leukemia," Blood 125, 2336-2343 (2015).
Spence, S. et al., "Targeting Siglecs with a sialic acid-decorated nanoparticle abrogates inflammation," Sci. Transl. Med., 7 303ra140 (2015).
English Translation of Office Action from Chinese Application No. 201780071459.2 dated Dec. 3, 2020.

* cited by examiner

MULTIPLEXED IMMUNE CELL ASSAYS ON A MICROPILLAR/MICROWELL CHIP PLATFORM

CROSS REFERENCE TO RELATED APPLICATIONS

This application claims the benefit of Provisional Application No. 62/570,965 filed on Oct. 11, 2017, and is hereby incorporated by reference in its entirety into this application.

BACKGROUND

Studying an organism's immune response is important to developing and improving biomedical applications—for example, vaccines, treatments for autoimmune diseases and allergies, and immunotherapies for cancer. These applications often involve enhancing, suppressing, or qualitatively shaping the immune response with ligands—in other words, molecules that bind to immune cells that trigger an immune response. For example, the surfaces of B-cells (an immune cell) are coated with antibodies that, when stimulated, will release and counteract the harmful molecules. In addition, T-cells (an immune cell), when stimulated, will secrete cytokines, which also counteract harmful molecules. Knowledge and development of practical therapeutic approaches are still very limited because there are many, diverse types of immune cells and potential ligands, but the potential for effective applications is high. One limiting factor in developing these applications is that, given the heterogeneity of immune cells and ligands, studying the effects of these ligands typically requires voluminous and often tedious laboratory testing.

Current immune cell assays are not capable of efficiently testing this complex immune response environment. Most assays are costly, low-throughput, and use large amounts of cells and reagents, which leads to expensive, inaccurate, and inefficient testing. For example, currently, immune cell surface markers are monitored by flow cytometry, and the cellular secreted markers are monitored by either ELISA or protein microarray methods separately. These methods often require repeated centrifuging, pipetting, and washing, which makes them inconvenient, low-throughput, and inefficient, resulting in lost cells and media. Further, antibody microarrays are currently available using glass slides (e.g., RayBio® glycobiology arrays and Eve Technologies 32-plex mouse cytokine arrays), but they have shortcomings, including that the biological samples must be manually collected and then further analyzed using the protein microarrays, they are not in situ, and they predominantly use 2D-cultured immune cells, which may not mimic immune cells in 3D-structured tissues in vivo. In addition, conventional glycoarrays on glass slides do not accommodate delicate ligands due to their instability in a dry condition. Accordingly, there is a need for an improved, rapid, multiplexed, and sensitive functionality assay to effectively monitor the immune cell responses to different ligands.

SUMMARY

The present invention is directed to a multiplexed method of monitoring immune-cell responses to different ligands, comprising dispensing immune cells onto at least one micropillar on a micropillar chip, and inserting the at least one micropillar into at least one microwell on a microwell chip, in which the at least one microwell contains at least one test compound.

The present invention is further directed to a multiplexed method of monitoring immune-cell responses to different ligands, comprising immobilizing antibodies onto at least one micropillar on a micropillar chip, and inserting the at least one micropillar into at least one micropillar chip, in which the at least one microwell contains a test compound.

These and other features, aspects, and advantages of the general inventive concepts will become better understood with reference to the following description and appended claims.

DETAILED DESCRIPTION

Figure 1A:
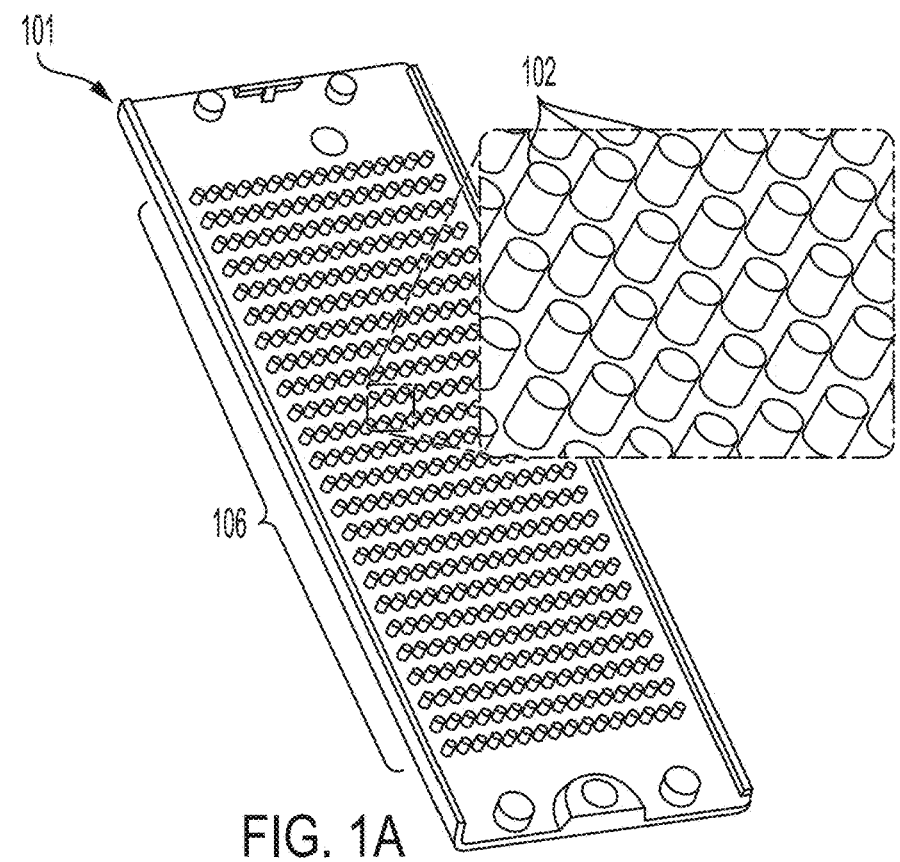
FIG. 1A shows an embodiment of a micropillar chip.
Figure 1B:
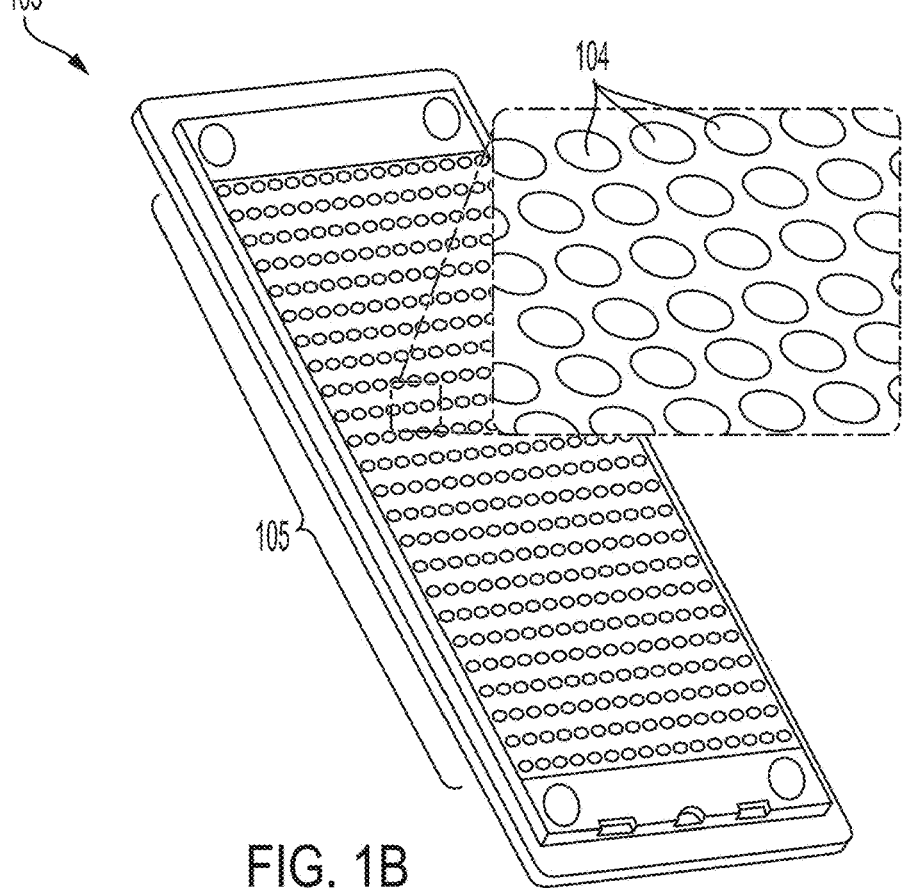
FIG. 1B shows an embodiment of a microwell chip.
Figure 2:
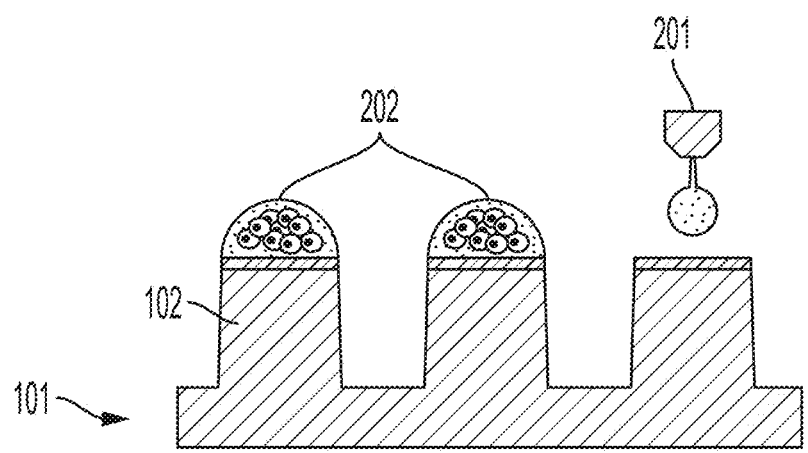
FIG. 2 shows a sectional view of an embodiment of a micropillar chip with immune cells on it.

While various exemplary embodiments and methods are described herein, other embodiments, methods, and materials similar or equivalent to those described herein are encompassed by the general inventive concepts. All references cited herein, including published or corresponding U.S. or foreign patent applications, issued U.S. or foreign patents, and any other references, are each incorporated herein by reference in their entireties, including all data, tables, figures, and text presented in the cited references.

Unless defined otherwise, all technical and scientific terms used herein have the same meaning as commonly understood by one of ordinary skill in the art to which the invention belongs.

All percentages, parts, and ratios as used herein are by weight of the total formulation, unless otherwise specified. All such weights as they pertain to listed ingredients are based on the active level and, therefore, do not include solvents or by-products that may be included in commercially available materials, unless otherwise specified.

All references to singular characteristics or limitations of the present disclosure shall include the corresponding plural characteristic or limitation, and vice versa, unless otherwise specified or clearly implied to the contrary by the context in which the reference is made.

The methods and embodiments of the present disclosure can comprise, consist of, or consist essentially of the essential elements of the disclosure as described herein, as well as any additional or optional element described herein or which is otherwise useful in carrying out the general inventive concepts.

To the extent that the terms "includes," "including," "contains," or "containing" are used in the specification or the claims, they are intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto."

All combinations of method or process steps as used herein can be performed in any order, unless otherwise specified or clearly implied to the contrary by the context in which the referenced combination is made.

All ranges and parameters, including but not limited to percentages, parts, and ratios, disclosed herein are understood to encompass any and all sub-ranges assumed and subsumed therein, and every number between the endpoints. For example, a stated range of "1 to 10" should be considered to include any and all sub-ranges beginning with a minimum value of 1 or more and ending with a maximum value of 10 or less (e.g., 1 to 6.1, or 2.3 to 9.4), and to each integer (1, 2, 3, 4, 5, 6, 7, 8, 9, and 10) contained within the range.

The general inventive concepts are directed to a method of performing multiplexed immune cell assays on a micropillar/microwell chip platform. These methods allow high-throughput assays for analyzing in situ immune cell responses to biologically active ligands, including, but not limited to, detection of secreted molecules, cell-surface marker expression, and intracellular marker expression.

Microarray 3D bioprinting refers to dispensing very small amounts of cells along with other biological samples such as hydrogels, growth factors, extracellular matrices, biomolecules, drugs, DNAs, RNAs, viruses, bacteria, growth media, or combinations thereof, onto a micropillar [102] on a micropillar chip [101] or into a microwell [104] on a microwell chip [103] using a microarray spotter [201] and then incubating the cells to create a mini-bioconstruct.

Since micropillar/microwell chip platforms [101, 103] (also known as "microarray biochips") contain arrays [105, 106] of up to 5,000 micropillars/microwells [102, 104], this method is ideal for high throughput testing.

According to one of the general inventive concepts disclosed herein, immune cells [202] may be encapsulated in a hydrogel, then deposited onto one or more micropillars [102] on a micropillar chip [101] using a microarray spotter [201], for example. According to another of the general inventive concepts disclosed herein, antibodies [501] may be uniformly immobilized on one or more micropillars [102] on a micropillar chip [101] (see FIG. 5). One or more biological samples (or test compounds) may then be deposited into one or more microwells [104] on a microwell chip [103]. The micropillar chip [101] containing micropillars [102] with encapsulated immune cells [202] or antibodies [501] may then be sandwiched with the microwell chip [103]. The micropillar chip [101] may then be removed and any molecular interactions may be examined through a variety of assays.

These and additional inventive concepts will be discussed in further detail below.

The Micropillar/Microwell Chip Platform

A microwell [104], as used in this invention, is a miniscule reservoir. In some exemplary embodiments, the microwell [104] is from about 0.3 mm in width, about 0.3 mm in length, and about 0.3 mm in height to about 2 mm in width, about 2 mm in length, and about 2 mm in height. In some further exemplary embodiments, the microwell [104] may be from about 0.3 mm in diameter and 0.3 mm in height to about 2 mm in diameter and about 2 mm in height. In some further exemplary embodiments, the microwell [104] is about 1.2 mm in diameter and about 1.5 mm in height. The microwell may be any shape suitable for the methods described herein. The microwell volume may be from about 30 nL to about 4 µL.

The microwell [104] may be housed on a microwell chip [103] that contains an array of microwells [105]. For example, a microwell chip [103] may contain an array of up to about 5,000 microwells. In some exemplary embodiments, the microwell chip [103] may contain about 100 to about 5,000 microwells [104]. In some exemplary embodiments, the microwell chip may contain about 100 to about 1,000 microwells. In some exemplary embodiments, the microwell chip may contain about 100 to about 900 microwells. In some exemplary embodiments, the microwell chip may contain about 200 to about 800 microwells. In some exemplary embodiments, the microwell chip may contain about 300 to about 700 microwells. In some exemplary embodiments, the microwell chip may contain about 300 to about 600 microwells. In some exemplary embodiments, the microwell chip may contain about 500 to about 600 microwells. In some exemplary embodiments, the microwell chip [103] may be from about 75 by 25 mm to 128 by 86 mm. The microwell chip [103] may be made of a biocompatible polymer. The biocompatible polymer may be clear or opaque depending on the type of analysis to be performed. For example, in some exemplary embodiments, the microwell chip [103] may be made of clear polystyrene or polydimethylsiloxane (PDMS). Examples of microwell chips include the S+ Microwell Chip made by Samsung Electro Mechanics, Co. and the MBD-W532A made by MBD Korea Co., Ltd.

A micropillar [102] may be housed on a micropillar chip [101] that contains an array of micropillars [106]. For example, a micropillar chip [101] may contain an array of up to about 5,000 micropillars. In some exemplary embodiments, the micropillar chip may contain about 100 to about 5,000 micropillars. In some exemplary embodiments, the micropillar chip may contain about 100 to about 1,000 micropillars. In some exemplary embodiments, the micropillar chip may contain about 100 to about 900 micropillars. In some exemplary embodiments, the micropillar chip may contain about 200 to about 800 micropillars. In some exemplary embodiments, the micropillar chip may contain about 300 to about 700 micropillars. In some exemplary embodiments, the micropillar chip may contain about 500 to about 600 micropillars. In some exemplary embodiments, the micropillar chip [101] may be from about 75 by 25 mm to 128 by 86 mm. The micropillar chip [101] may also be made of a biocompatible polymer. The biocompatible polymer may be clear or opaque depending on the type of analysis to be performed. For example, in some exemplary embodiments, the micropillar chip may be made of clear polystyrene or polydimethylsiloxane (PDMS). The micropillar's size corresponds to the size of a corresponding microwell [104] so that it may fit inside the microwell. The micropillar may be any shape suitable for the methods described herein. In some exemplary embodiments, about 100 pL to about 100 nL of at least one biosample may be printed onto a micropillar [102].

Encapsulating Immune Cells and Dispensing on Micropillars

In some embodiments, immune cells [202] may be dispensed onto one or more micropillars [102] on a micropillar chip [101].

To create a 3D-bioconstruct of the immune cells for dispensing onto the micropillars [102], the cells may be encapsulated in a hydrogel. A hydrogel is generally a polymer that contains water. For example, suitable hydrogels may be alginate, methacrylated alginate, chitosan, hyaluronic acid, fibrinogen, collagen, methacrylated collagen, PuraMatrix, Matrigel, PepGel, and polyethylene glycol. Optionally, additional biomolecules may be added to the cell-suspensions. Biomolecules may include molecules that support cellular or tissue growth, such as extracellular matrices (ECMs), growth factors, peptides, and carbohydrates. Biomolecules may also include any molecules chosen to mimic a particular biological environment, such as a particular tissue (liver, heart, brain, etc.). In some exemplary embodiments, the biomolecules may be, for example, collagen I and IV, laminin, and fibronectin for ECMs, hepatocyte growth factor (HGF), epidermal growth factor (EGF), and basic fibroblast growth factor (bFGF) for growth factors, tethered RGDS (Arg-Gly-Asp-Ser) and YIGSR (Tyr-Ile-Gly-Ser-Arg) for peptides, and heparin and methacrylated heparin for carbohydrates. The cell concentration of the encapsulated immune-cell suspension may be from about 10,000 to about 20 million cells/mL, about 500,000 to about 5 million cells/mL, or about 0.1 million to about 2 million cells/mL. The hydrogel may be from about 0.1 w/v % to about 10 w/v % of the final cell-suspension.

In some exemplary embodiments, the immune-cell suspension [202] may be printed onto the micropillar [102] by a microarray spotter [201]. A microarray spotter [201] is a robotic liquid dispensing system capable of printing small amounts of biological samples, also known as "spots," onto a micropillar [102] or into a microwell [104] ("printing"). In some exemplary embodiments, the microarray spotter [201] may be capable of printing spots onto multiple micropillars [102] on the same micropillar chip [101] to facilitate high-throughput testing. The microarray spotter [201] may be capable of printing from about 20 nL to about 200 nL of immune-cell suspension [202] onto the micropillars [102].

Exemplary microarray spotters include S+ Microarrayer, commercially available from Samsung and MicroSys, PixSys, and CellJet, commercially available from DigiLab.

To facilitate attachment of the immune-cell suspension [202] onto the micropillar chip, the surface of the micropillar chip [101] may be treated. For example, the surface of the micropillar chip [101] may be treated by coating the surface with reactive polymers [301]. Suitable reactive polymers [301] may include poly(maleic anhydride-alt-1-octadecene) (PMA-OD), poly(styrene-co-maleic anhydride), polydopamine, and polyhydroxyethylmethacrylate. In some exemplary embodiments, the micropillar chip may be coated with 0.001%-0.1% PMA-OD.

Figure 3A:
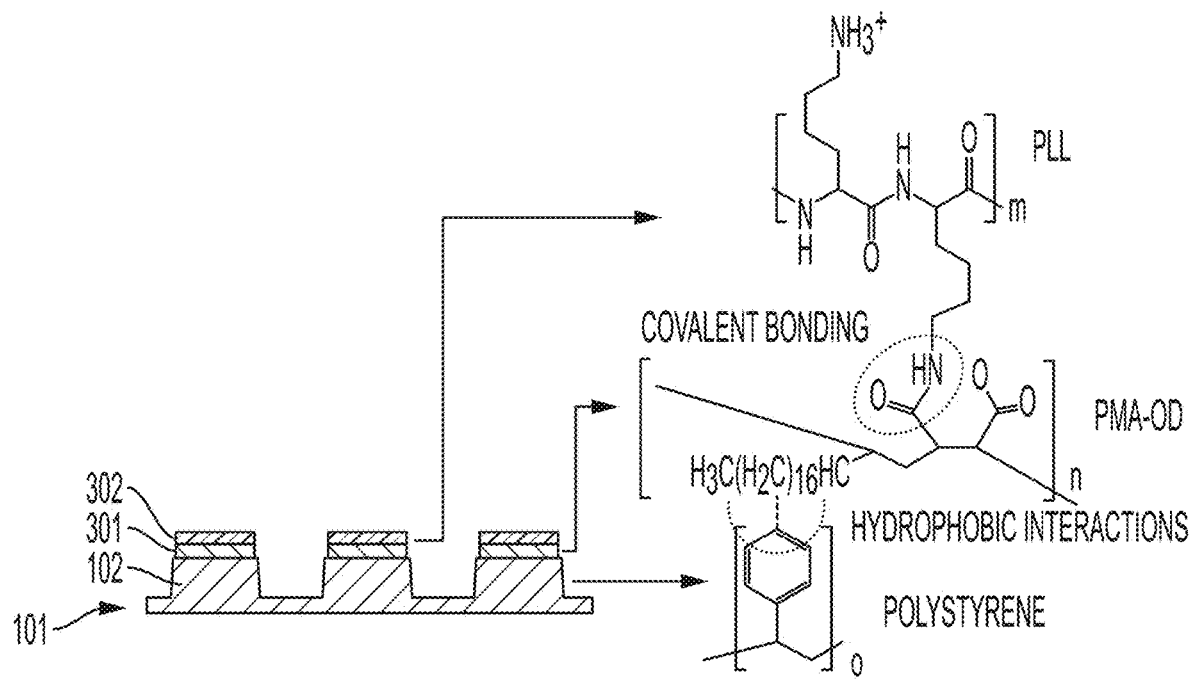
FIG. 3A shows the chemistry of the reactive polymers and micropillar plate.
Figure 3B:
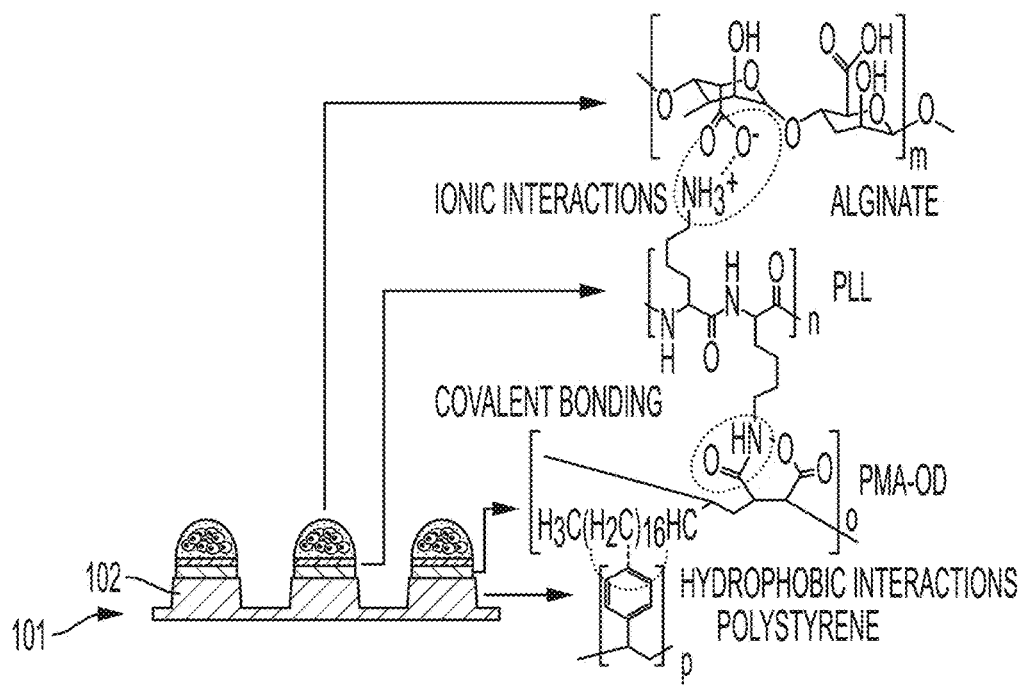
FIG. 3B shows the chemistry of the reactive polymers, micropillar plate, and immune-cell suspension.

The surface may then be further treated by dispensing a mixture of poly-L-lysine (PLL) and $BaCl_2$ or $CaCl_2$ [302] onto the micropillars [102]. For example, in some exemplary embodiments, a mixture of 0.0033% PLL and 16.6 mM $BaCl_2$ may be printed onto the micropillars [102] using a microarray spotter [201] or a multichannel pipette. The bonding chemistry related to an exemplary embodiment of treating the micropillar surface for facilitating attachment of immune-cell suspension is shown in FIG. 3. In addition to PLL-$BaCl_2$ printing, other biomolecules such as Matrigel can be printed to facilitate cell spot attachment and cell growth.

After treating the micropillar surface (see, e.g., FIG. 3), the immune-cell suspension [202] may be dispensed onto the micropillars [102]. In some exemplary embodiments, the immune-cell suspension [202] is printed onto the micropillars [102] using a microarray spotter [201]. The amount of immune-cell suspension dispensed should correspond to the size of the micropillar [102]. In some exemplary embodiments, about 20 nL to about 200 nL of immune-cell suspension may be dispensed onto the micropillars [102].

In exemplary embodiments wherein PLL and $BaCl_2$ are used to facilitate immune-cell suspension attachment and wherein alginate is used as a hydrogel in the immune-cell suspension, a strong gel is formed via crosslinking between the carboxylic acids in the alginate and the divalent metal ions ($Ba^{2+}$). In addition to the ionic crosslinking with alginate and $BaCl_2$, immune cells may be printed and gelled in multiple layers by various crosslinking mechanisms, including photo (e.g., oxidized methacrylated alginate), salt (e.g., PuraMatrix), enzyme (e.g., fibrinogen), temperature (Matrigel), and linkers (e.g., streptavidin and biotin).

Modulating the Immune Cells

Figure 4:
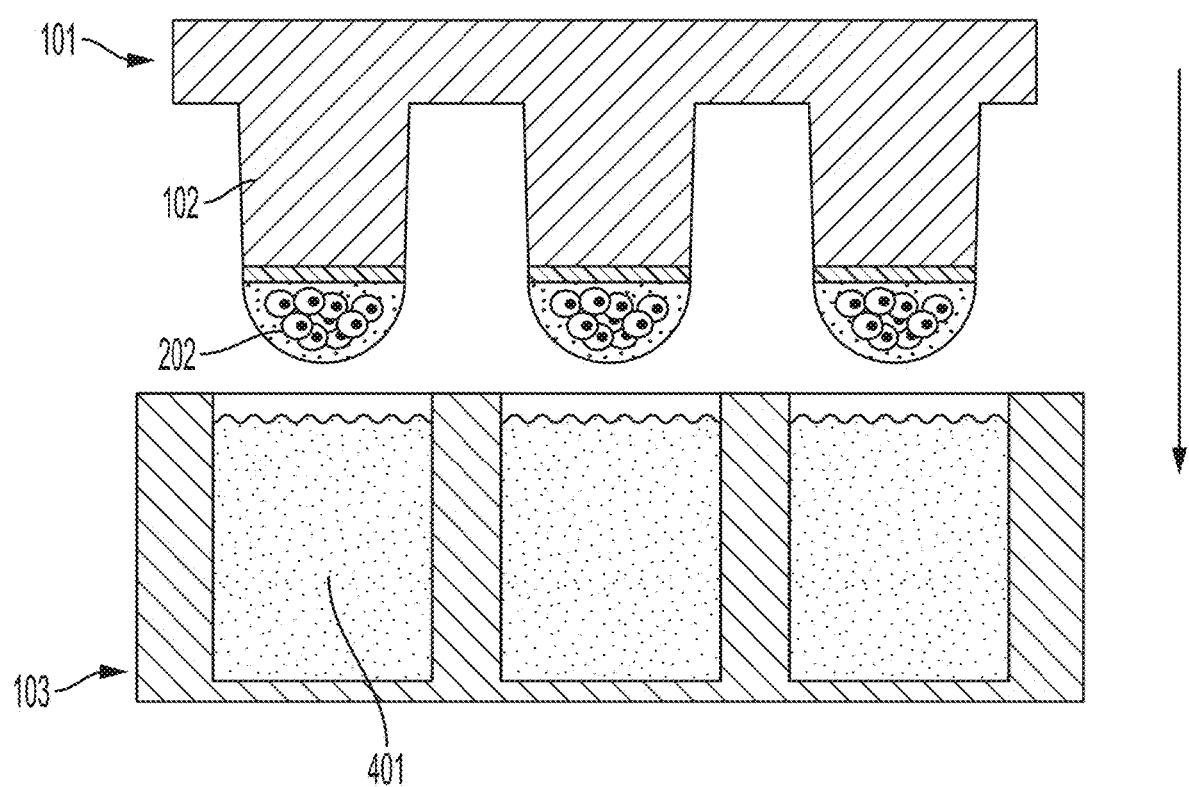
FIG. 4 shows a sectional view of an embodiment of micropillars containing cells and an embodiment of microwells containing growth media.

In some exemplary embodiments, after the immune cells [202] are encapsulated onto the tips of the micropillars [102] on a micropillar chip [101], the micropillar chip [101] may be sandwiched with a corresponding microwell chip [103] that contains growth media [401] (see, e.g., FIG. 4) for incubation.

Growth media is generally a liquid designed to support cell growth. Suitable examples of growth media may include Dulbecco's Modified Eagle Medium (DMEM), Roswell Park Memorial Institute medium (RPMI), and William's E. In some exemplary embodiments, the growth media may be supplemented with biomolecules. In some exemplary embodiments, the biomolecules may be, for example, ECMs, growth factors, fetal bovine serum (FBS), L-glutamine, glucagon, hydrocortisone, insulin, commercial maintenance supplements, and antibiotics such as penicillin-streptomycin (P/S). Growth media may be easily replaced, if necessary, by sandwiching the micropillar chip [101] with fresh growth media in a new microwell chip [103].

Figure 7:
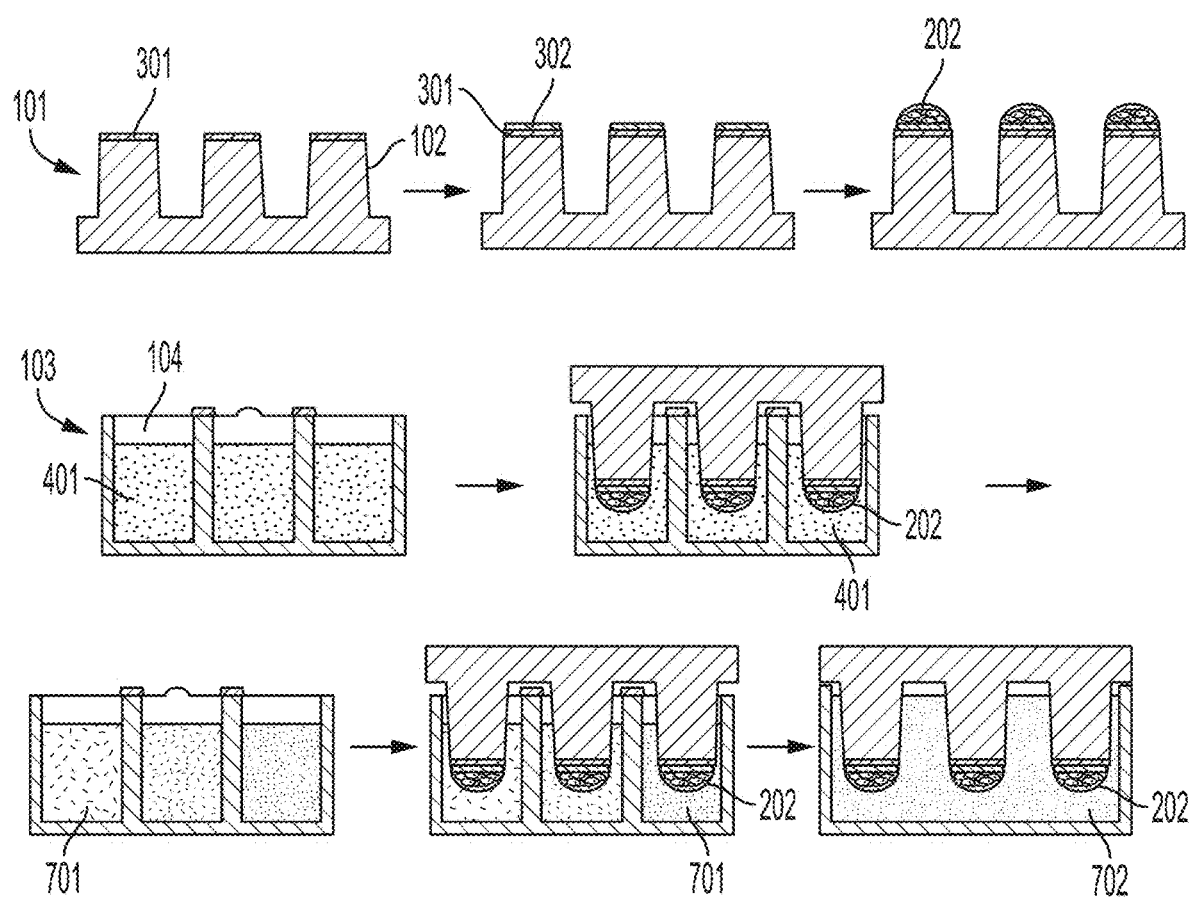
FIG. 7 is a flow diagram demonstrating the method used in Example 1.

In some exemplary embodiments, after the immune cells have been incubated, the micropillar chip [101] containing the immune cells may be sandwiched with a microwell chip [103] containing test compounds [701] (see, e.g., FIG. 7). Test compounds may include any biomolecules that may aid in analyzing immune-cell activity, such as, but not limited to, intracellular biomarker expression, cell-surface biomarker expression, soluble factor secretion, cytotoxicity, cell growth, cell viability, and cell differentiation. Test compounds may include, but are not limited to, bioactive carbohydrates, such as natural and synthetic glycoproteins, glycolipids, polysaccharides, oligosaccharides, glycoconjugates like glycopolymers (e.g., glucosyl polymer, galactosyl polymer, mannosyl polymer, GlcNAc polymer, lactosyl polymer, α2,3-sialopolymer, α2,6-sialo polymer, α2,8-sialopolymer, etc.), pathogens (e.g., virus, bacteria and bacterial toxins, such as lipopolysaccharide (LPS)), and allergenic compounds such as sulindac and nitrofurantoin.

In some exemplary embodiments, after the micropillar chip [101] with immune cells [202] has been exposed to test compounds [701], the immune cells [202] may be stained for high-content imaging. In some exemplary embodiments, this is carried out by sandwiching the micropillar chip [101] with a microwell chip [103] containing at least one staining dye [702].

Examples of staining dyes and the cellular processes that they may indicate are known in the art, including calcein AM and ethidium homodimer-1 for cell viability and cytotoxicity; Hoechst 33342 for changes in nuclear function; YO-PRO-1/propidium iodide for apoptosis or necrosis; tetramethyl rhodamine methyl ester (TMRM) for mitochondrial membrane potential; fluo-4 AM for intracellular calcium levels; and monochlorobimane (MCB) and thiol green dye for glutathione levels. Cells may also be stained with recombinant viruses carrying genes for various fluorescent biomarkers. Exemplary recombinant viruses are baculoviruses, for example Bac-to-Bac® baculovirus expression system from ThermoFisher. Other suitable staining methods may be known in the art. Examples of fluorescent biomarkers include blue fluorescent protein (BFP), green fluorescent protein (EGFP), orange fluorescent protein (mOrange), or red fluorescent protein (mCherry). In some further exemplary embodiments, the immune cells may be stained with primary antibodies with fluorescent tags (e.g., fluorescein isothiocyanate (FITC)-labeled rat anti-mouse CD40, CD1d, CD80, and I-A[d]).

Example 1

Figure 12:
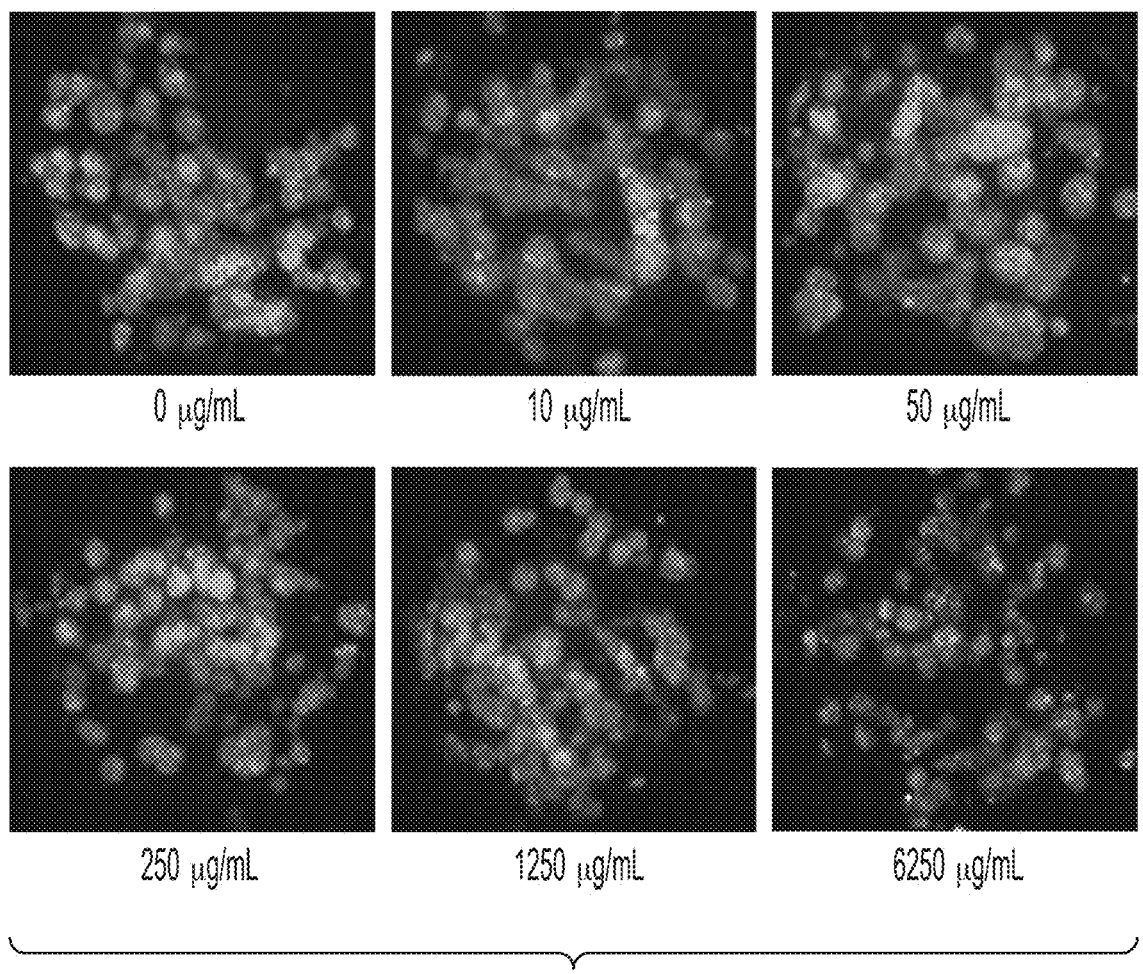
FIG. 12 are images of immune cells from Example 1.
Figure 13:
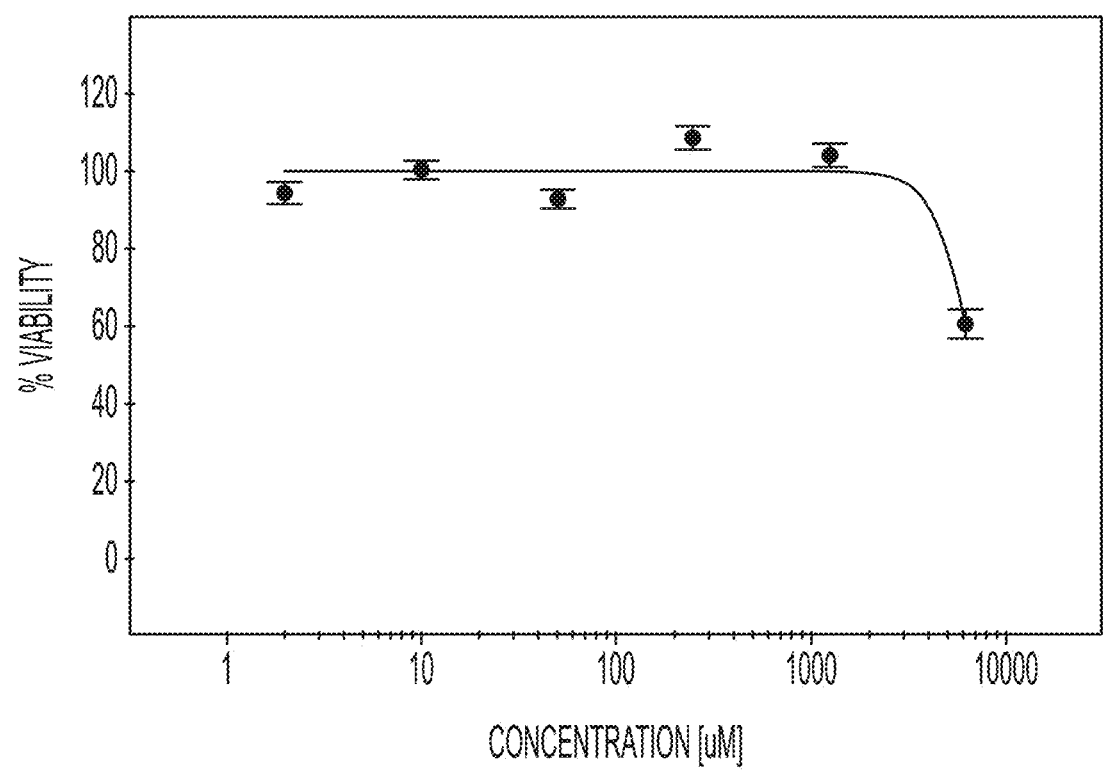
FIG. 13 is a graph showing results from Example 1.

FIGS. 7, 12, and 13 are discussed in this example. The following example demonstrates method of measuring cytotoxicity of immune cells exposed to N-α2,3-sialolactosyl polymer using an exemplary method of encapsulating and attaching immune cells to the micropillars.

RAW264.7 cells from ATCC were cultured in T-75 flasks with DMEM containing 25 mM glucose, 4.0 mM L-glutamine, 1 mM sodium pyruvate, 1% penicillin-streptomycin, and 10% fetal bovine serum.

A 384-pillar micropillar chip was coated with 0.01% PMA-OD [301], which was followed by spotting a mixture of 0.0033% PLL and 16.6 mM $BaCl_2$ [302] on the tips of the micropillars [102] using a microarray spotter (S+ MicroArrayer).

The micropillar chip containing immune cells was prepared by dispensing 60 nL of immune cell suspension (RAW 264.7 cells mouse macrophage cell line) in a mixture of 0.75% alginate and 1 mg/mL Matrigel (to a final seeding density of $3\times10^6$ cells/mL or 180 cells per micropillar) on top of the dried PLL-$BaCl_2$ layer.

After instantaneous alginate gelation, the micropillar chip was immediately sandwiched with the microwell chip [103] containing 950 nL of growth media (DMEM) [401] by aligning the edges of the chips, and then the sandwiched chip was incubated in a gas-permeable chamber with water in the $CO_2$ incubator at 37° C.

The encapsulated immune cells [202] were then exposed to N-α2,3-sialolactosyl polymer [701] at the concentration ranges of 0, 10, 50, 250, 1250, and 6250 µg/mL, as well as lipopolysaccharide (LPS) as a positive control at the concentration ranges of 0, 0.4, 2, 10, 50, 250 µg/mL (dissolved in growth media) for 48 hours, rinsed with 0.9% saline solution (140 mM NaCl and 20 mM $CaCl_2$), and stained with fluorescent dyes [702] (1 µM calcein AM and 1 µM ethidium homodimer for 1 hour for cell viability).

Fluorescent cell images were acquired from the micropillar chip using an automated fluorescent microscope (S+ Scanner), and dosage response curves and $IC_{50}$ values were obtained. The images and data are shown in FIGS. 12 and 13. The light areas shown in FIG. 12 represent live RAW cell spheroids.

Immobilizing Antibodies on Micropillars

Figure 5A:
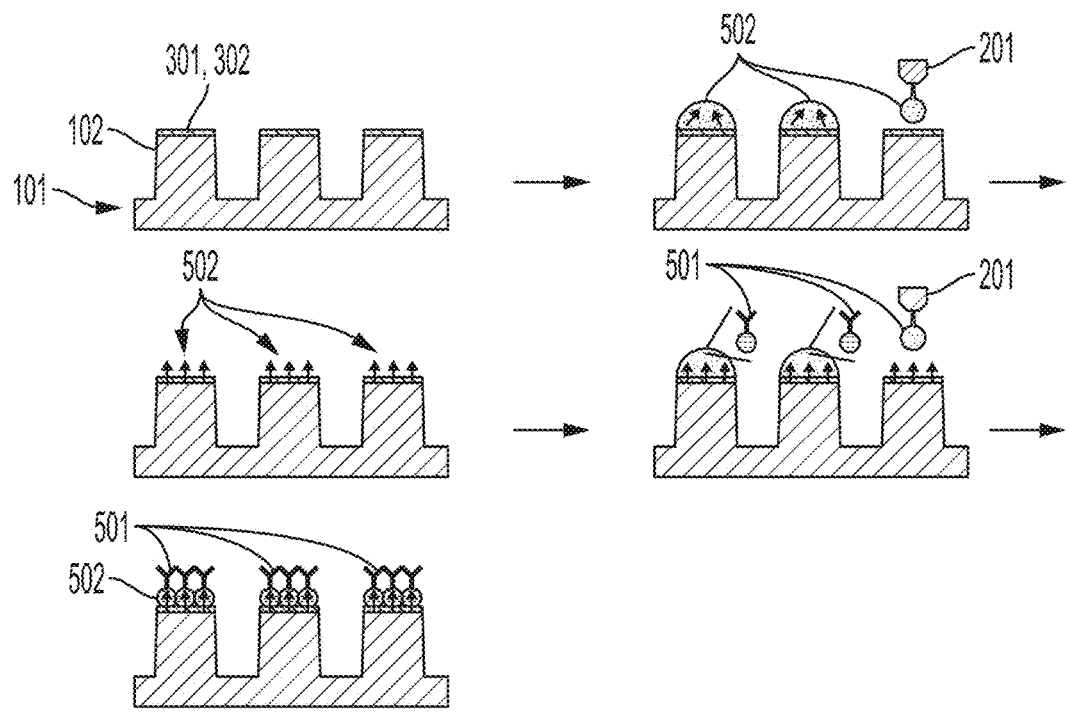
FIG. 5A is a flow diagram of an exemplary method of immobilizing antibodies on micropillars.
Figure 5B:
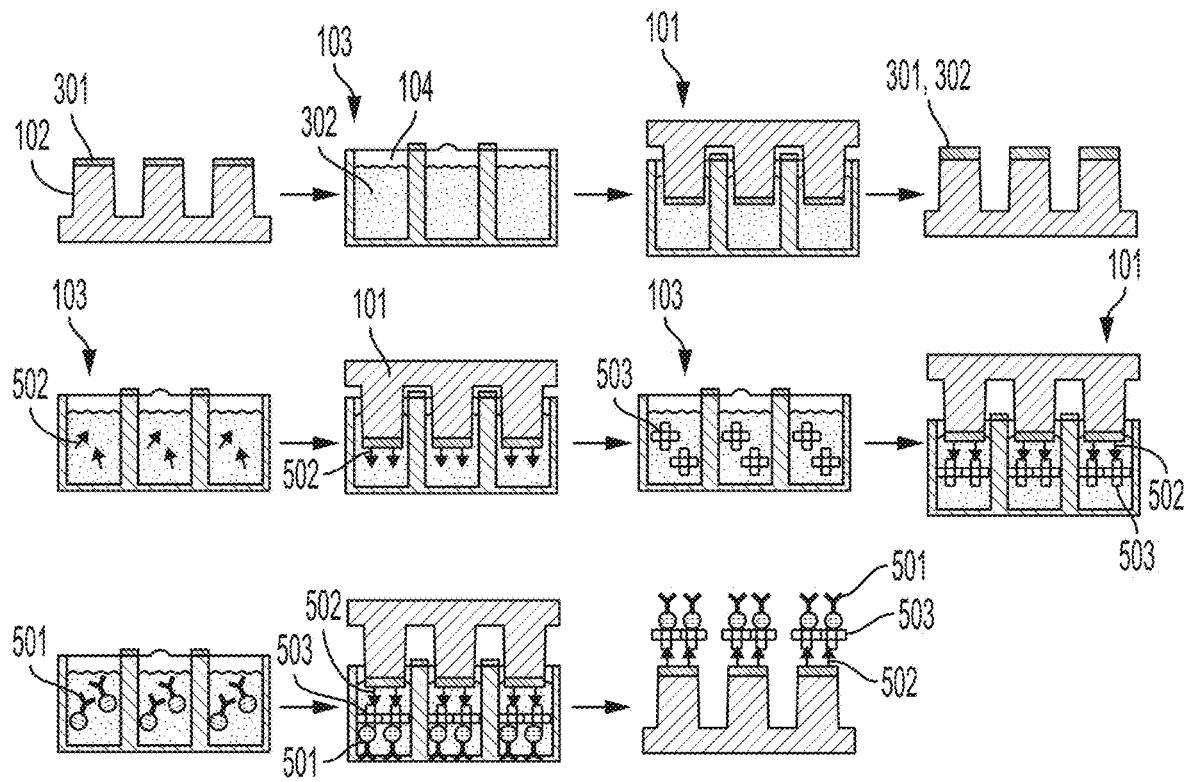
FIG. 5B is a flow diagram of an exemplary method of immobilizing antibodies on micropillars.

In some exemplary embodiments, antibodies [501] may be immobilized on micropillars [102] to detect molecules released by immune cells [202] (see FIGS. 5A-B).

To facilitate attachment of antibodies [501] on the micropillars [102] on a micropillar chip [101], the micropillar chip surface may be treated. For example, the micropillar chip surface may be coated with reactive polymers [301] (e.g., poly(maleic anhydride-alt-1-octadecene) (PMA-OD), poly (styrene-co-maleic anhydride) (PS-MA), and poly(isobutylene-alt-maleic anhydride) (PIMA)). The micropillar may be further treated with PLL [302] for covalent attaching of ligands. The reactive polymers may be dispensed onto the micropillars by printing with a microarray scanner, sandwiching the micropillars with microwells that contain the reactive polymers, or any other method known in the art.

Ligands [502] that aid in attaching antibodies may then be dispensed onto the PLL coating. Suitable ligands [502] may be, but are not limited to, sulfo-NHS-biotin, streptavidin, 3-carboxyphenyl boronic acid, and maleimide-PEG-COOH. Other ligands known in the art for aiding in attaching antibodies may also be used.

After dispensing ligands onto the polymer coating [301, 302], antibodies [501] with affinity tags may be dispensed onto the micropillars [102]. For example, in the embodiment using sulfo-NHS-biotin as the ligand, biotinylated antibodies may be printed onto the micropillars to interact with the ligands and be attached straightly on the surface of the micropillars (see, e.g., FIGS. 5A-B). In the embodiment using 3-caboxyphenyl boronic acid linker, the antibodies are immobilized through specific boronic acid-carbohydrate interaction. Specifically, the cis-diol of the carbohydrates in the Fc part of the antibody forms a covalent bond with boronic acid, which facilitates an oriented antibody immobilization on the micropillar surface.

Example 2

Figure 10A:
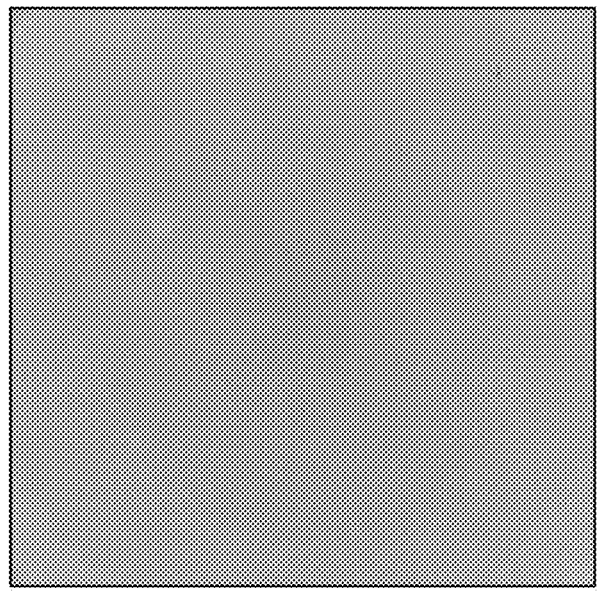
FIG. 10A is an image of the micropillar chip tested in Example 2 without PLL.
Figure 10B:
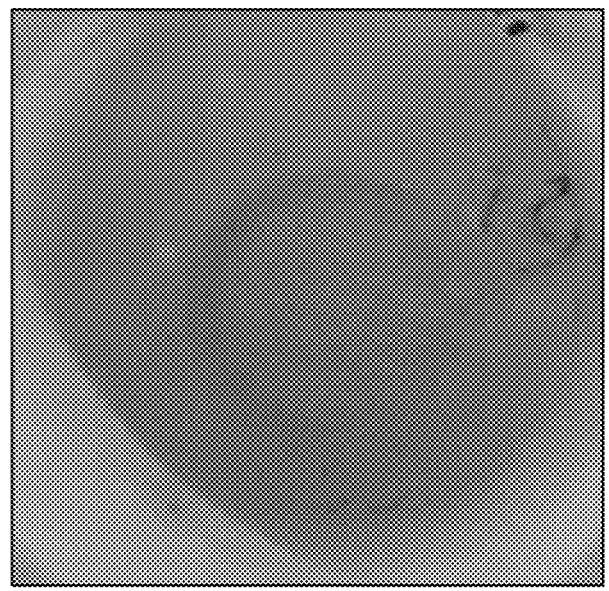
FIG. 10B is an image of the micropillar chip tested in Example 2 with PLL.
Figure 11:
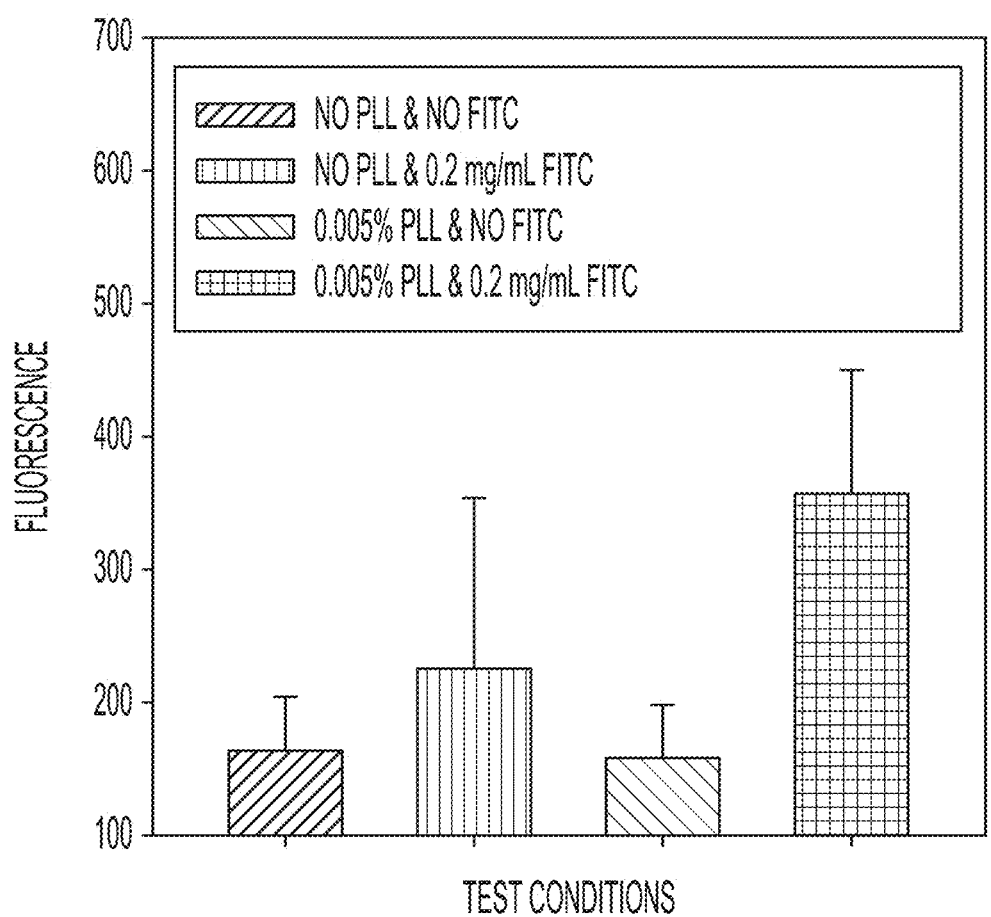
FIG. 11 is a bar graph showing results from Example 2.

FIGS. 10A-B and 11 are discussed in Example 2. Example 2 demonstrates an exemplary embodiment of treating the micropillars [102] on a micropillar chip [101] to facilitate the attachment of antibodies.

A 384-pillar micropillar chip was coated with 0.1% (w/v) PMA-OD [301] and reacted with 0.005% PLL [302], which was followed by reacting with 0.2 mg/mL of FITC. Controls were also prepared using no PLL and no FITC, no PILL and 0.005% PLL and no FITC. The micropillar chips were then imaged for fluorescence to assess to determine whether PLL can provide amine functionality.

FIGS. 10A-B and 11 show that the green fluorescent intensity increased in the presence of PLL, indicating that PLL can provide amine functionality, which can be used for sulfo-NHS-biotin. FIG. 10A shows the fluorescence of a micropillar treated with 0.2 mg/mL FITC in the absence of PLL, and FIG. 10B shows the fluorescence of a micropillar with 0.005% PLL and 0.2 mg/mL FITC.

Detecting Secreted Molecules Targeted by Antibodies

In some exemplary embodiments, the methods described above may be used to detect secreted molecules targeted by antibodies, such as antigens, growth factors (e.g., vascular endothelial growth factor (VEGF)) and cytokines (e.g., IL-1, IL-6, IL-8, IL-12, IL-18, TGF-β, TNF-α, INF-α, and IL-10). For example, an immune-cell suspension [202] may be made using a mixture of immune cells and a hydrogel as described above. The immune-cell suspension [202] may then be printed onto the micropillars [102] of a micropillar chip [101]. Next, the micropillar chip [101] may be sandwiched with a microwell chip [103] with microwells [104] containing growth media to allow antibody-targeted molecules [601] (e.g., antigens, cytokines, etc.) to be released by the immune cells. The growth media may optionally contain biomolecules, for example to induce the release of antibody-targeted molecules. Next, the micropillar chip [101] may be removed from the microwell chip [103].

Next, a micropillar chip [101] on which antibodies [501] have been attached, as described above (see, e.g., FIG. 5), may be sandwiched with the microwell chip [103] containing the antibody-targeted molecules [601]. After waiting an appropriate amount of time to allow the antibody-targeted molecules [501] to interact with the antibodies, the micropillar chip [101], containing antibodies and possibly antibody-targeted molecules that attached to the antibodies, may be removed and sandwiched with a microwell chip [103] with microwells [104] containing primary antibodies with fluorescent tags [602]. After allowing an appropriate amount of time to allow the antibody-targeted molecules [601] to interact with the primary antibodies with fluorescent tags [602], the micropillar chip [101] may be removed and analyzed via imaging, for example, by automated fluorescent microscopes or microtiter plate readers. The fluorescent intensity from the tags may be measured from the cells on the micropillar chip.

Example 3

Figure 17:
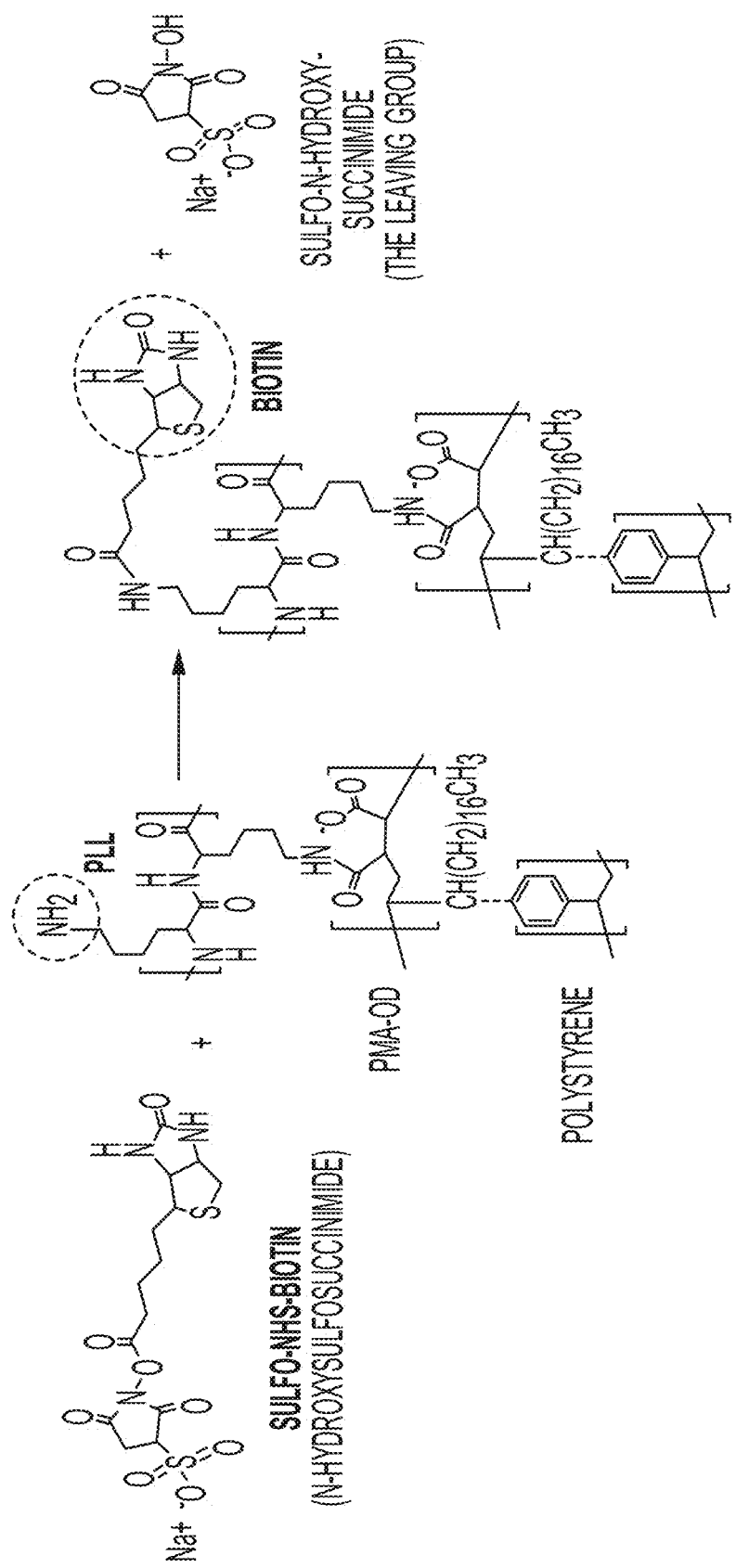
FIG. 17 shows the chemistry of the biotin-PLL attachment.
Figure 18:
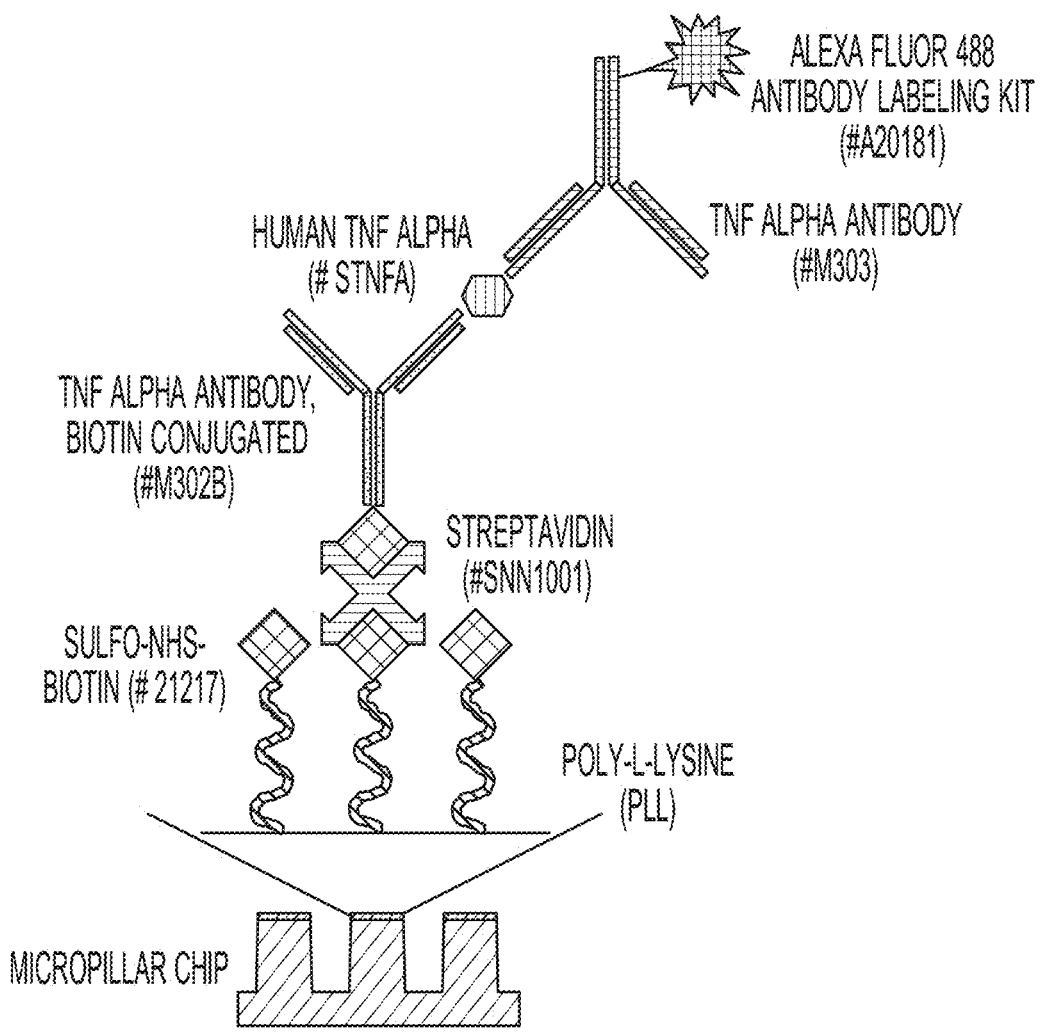
FIG. 18 shows attachment of biotin-conjugated antibodies through streptavidin-biotin interactions.

FIGS. 5B, 17, and 18 are discussed in Example 3. Example 3 demonstrates an exemplary embodiment of immobilizing antibodies on micropillars and detecting molecules targeted by those antibodies.

A 384-pillar micropillar chip was coated with 0.1% PMA-OD in ethanol and dried for 2 hours. Then the micropillars were reacted with 0.005% PLL in 20 mM sodium bicarbonate buffer for 4 hours in a microwell chip.

After rinsing the micropillar chip with distilled water (DW) twice for 10 minutes, covalently immobilized PLL was reacted with 5 mg/mL sulfo-NHS-biotin [502] in 150 mM Na$_2$HPO$_4$ (pH 8.5) in a microwell chip for 2 hours.

After rinsing with DW, 1 mg/mL streptavidin [503] in 150 mM Na$_2$HPO$_4$ (pH 8.5) was added in a microwell chip and then sandwiched with the micropillar chip [101] with PLL-biotin for 2 hours.

After rinsing, 5 μg/mL of capturing antibodies [501] conjugated with biotin (e.g., biotinylated TNF-α antibody, biotinylated IL-6 antibody, biotinylated IL-12 antibody, and biotinylated IL-10 antibody) in a blocking buffer (e.g., 1% BSA in PBS) were added on the micropillar chip [101] with PLL-biotin-streptavidin and incubated for 2 hours.

Figure 6:
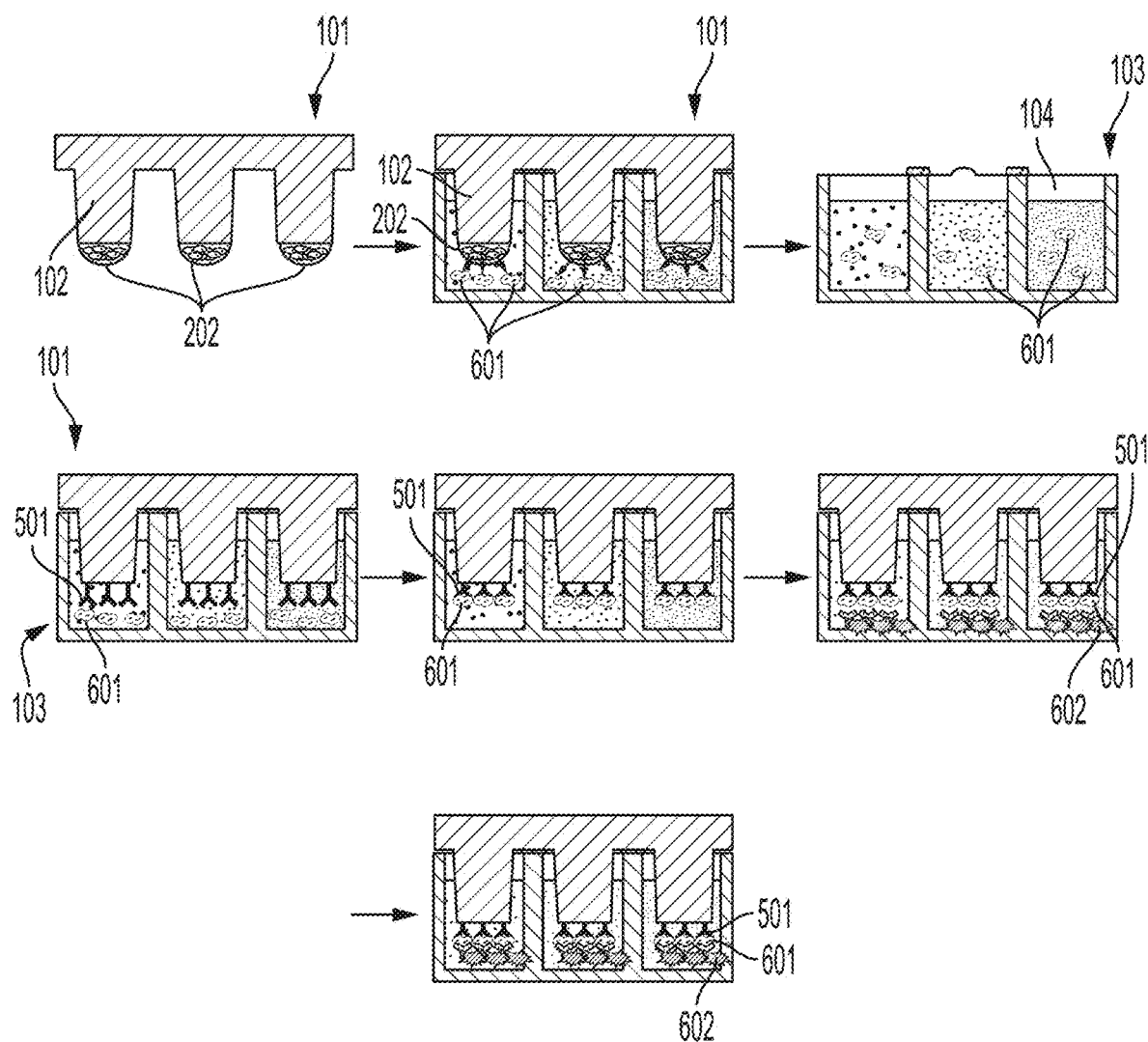
FIG. 6 is a flow diagram of an exemplary method of detecting antibody-targeted molecules.

The micropillar chips with capturing antibodies were then sandwiched with a microwell chip containing a cell supernatant with secreted cytokines (TNF-α, IL-6, 12, and 10) in the microwell chip (see, e.g., FIG. 6).

Next, the cytokines captured on the micropillar chip were stained with fluorescently labeled primary antibodies (FITC-labeled TNF-α antibody) (see, e.g., FIG. 18) in microwells, followed by rinsing, washing, and drying. Finally, fluorescent images on the micropillars were acquired from the chip using the S+ scanner, and dosage response curves were obtained.

Example 4

3-Carboxyphenyl boronic acid (3-CPBA) was dispensed on the micropillar for oriented immobilization of primary antibody. 3-CPBA may be conjugated with amine groups from PLL on the micropillar via amide bond formation.

3-CPBA (400 mM) was dissolved in 50 mM 2-(N-morpholino)ethane sulfonic acid buffer (IVIES; pH 6.0.) in a glass vial. To this mixture, N-(3-(dimethylamino)propyl)-N-ethylcarbodiimide hydrochloride (EDC; 80 μM) was added and allowed to react for 4 hours at room temperature. Next, 950 nL of this mixture was printed into a microwell chip. The PLL-coated micropillar chip was sandwiched with the microwell and incubated for 4 hours at room temperature, followed by rinsing and drying. The 3-CPBA modified micropillar was then sandwiched with another microwell containing capturing antibody (TNF-α antibody, IL-6 antibody, IL-12 antibody, and IL-10 antibody) in Tris-HCl solution (2 mM, pH 9) at 4° C. for 24 hours, followed by rinsing with Tris-HCl and distilled water (DW) to remove unbound antibodies.

The micropillar chip containing capturing antibodies was sandwiched with the microwell plate containing cell supernatants at 4° C. for 24 hours, followed by rinsing with Tris-HCl and DW to remove unbound analytes. The micropillar chip was stained with FITC-labeled secondary antibodies (TNF-α antibody, IL-6 antibody, IL-12 antibody, and IL-10 antibody) at 4° C. for 6 hours, then rinsed with TBS twice for 10 minutes, and dried. Finally, fluorescent images were acquired from the micropillar chip using the S+ scanner for image analysis and data extraction.

Measuring Surface Biomarker Expression in Immune Cells

Figure 8:
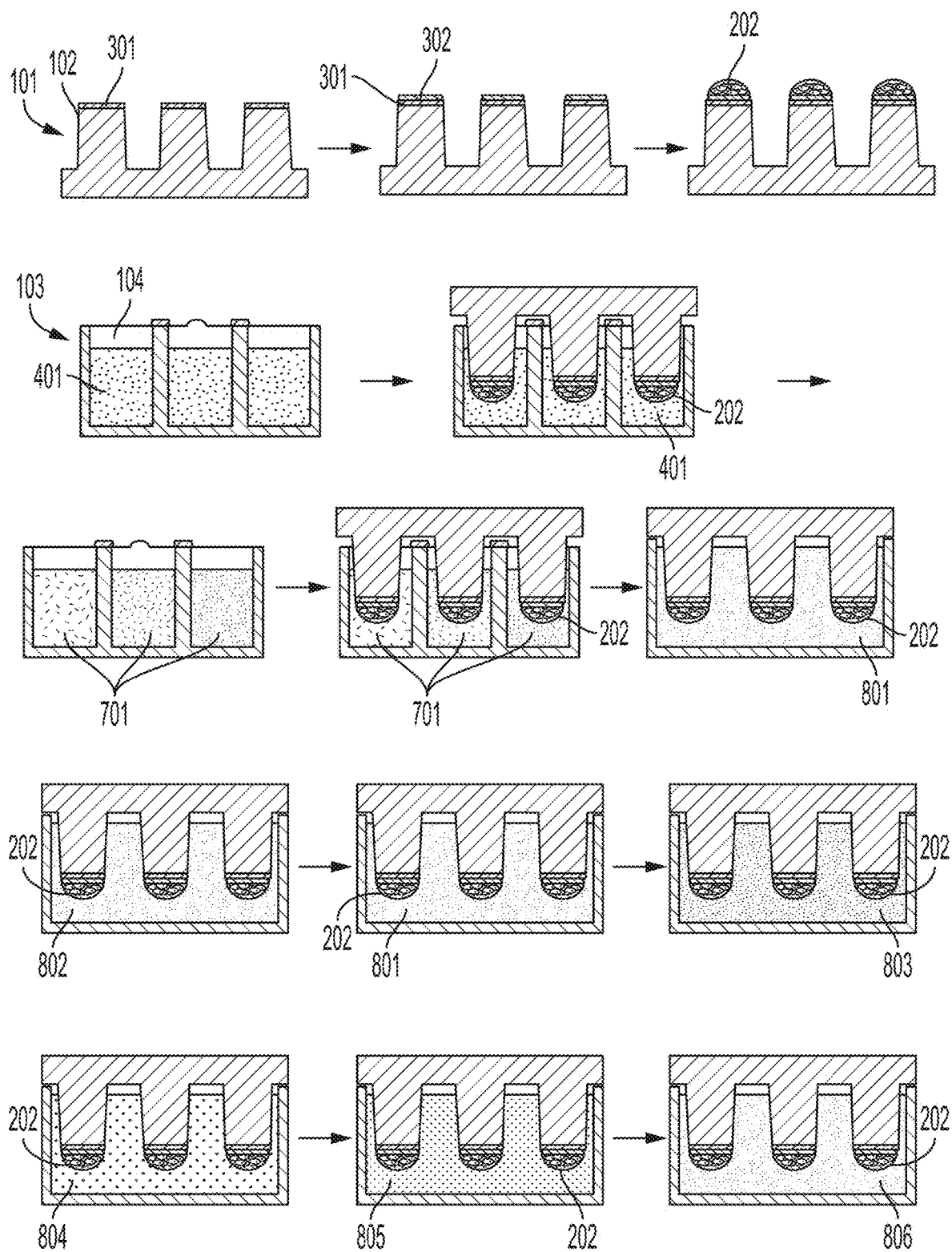
FIG. 8 is a flow diagram demonstrating the method used in Example 5.
Figure 9:
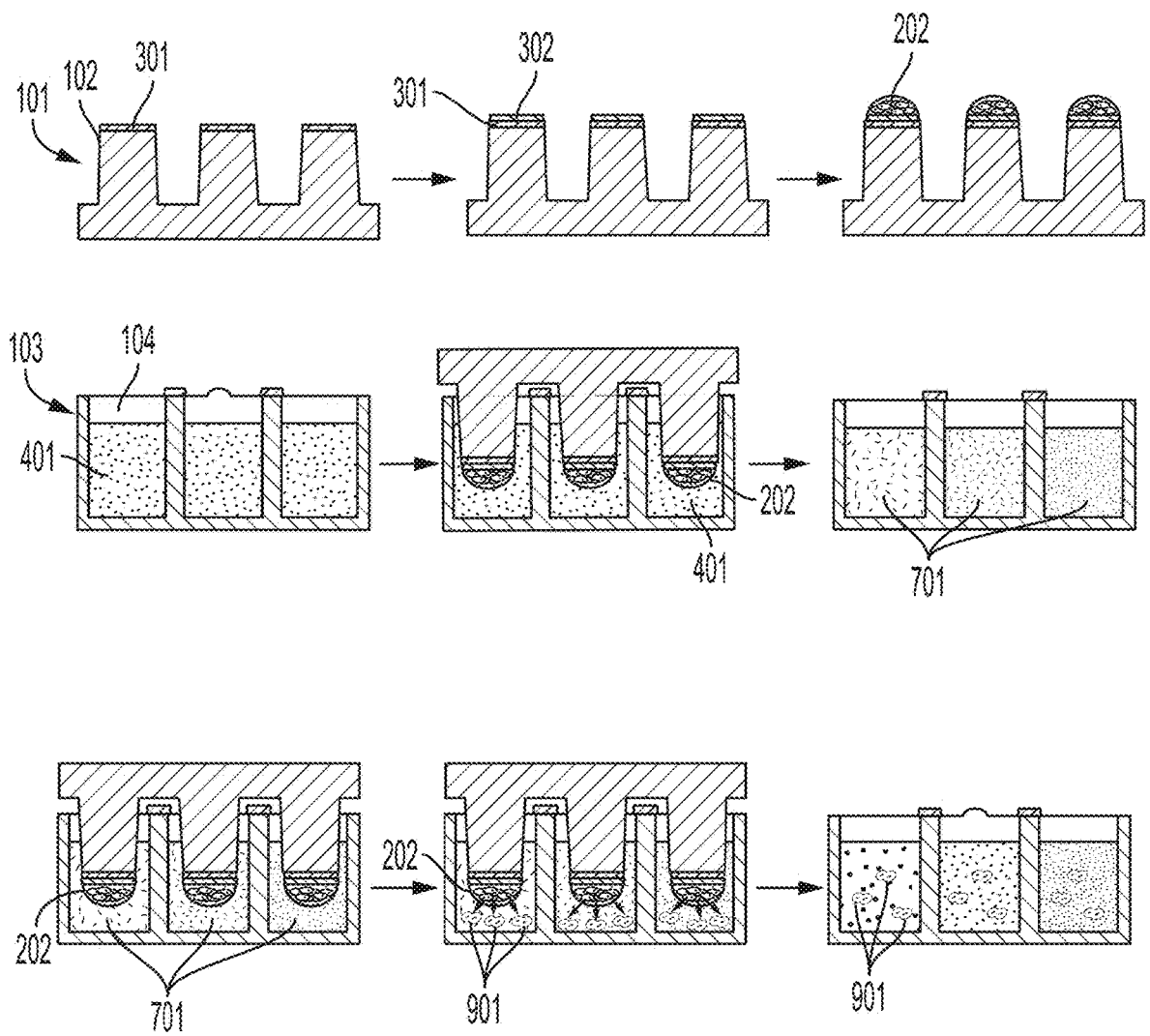
FIG. 9 is a flow diagram demonstrating an exemplary method of measuring soluble factor secretion.

The general methods discussed above may be used to measure changes in the expression levels of cell surface markers before and after treatment with test compounds. This is generally done by printing immune cells [202] onto the micropillars [102] of a micropillar chip [101], exposing the immune cells [202] to test compounds [701], staining the cells with primary antibodies [804], and then imaging the cells to detect changes in expression levels of cell surface markers. FIG. 8 describes a general exemplary embodiment of this method.

Example 5

Figure 14A:
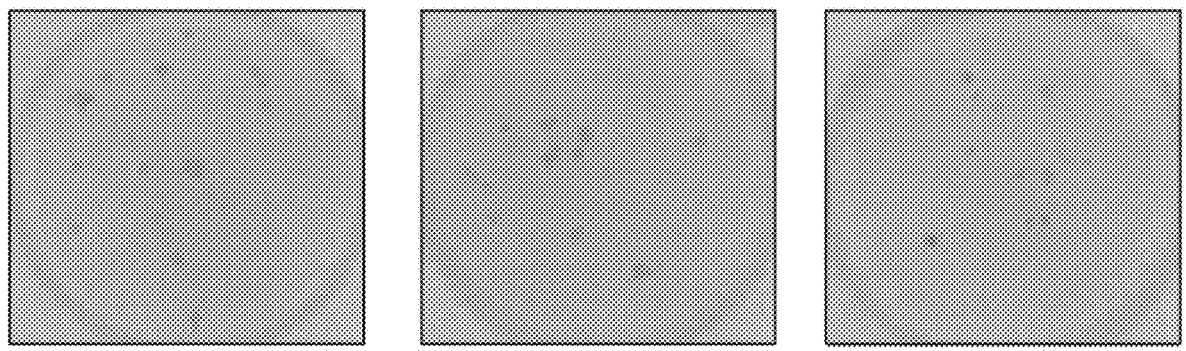
FIG. 14A is images of immune cells from Example 5.
Figure 14B:
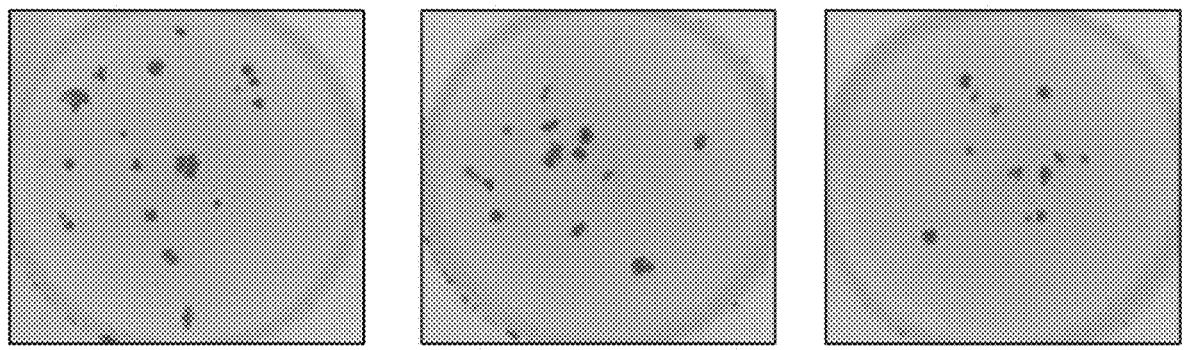
FIG. 14B is images of immune cells from Example 5.

FIGS. 8, 14, and 15 are discussed in Example 5. Example 5 demonstrates an exemplary embodiment of measuring surface biomarker expression in immune cells using the micropillar/microwell chip platform.

The micropillars of a 384-pillar micropillar chip were coated with 0.01% PMA-OD. Then 16.6 mM $BaCl_2$/0.0033% PLL were printed onto the micropillars using a microarray scanner.

An immune-cell suspension was prepared using 0.75% alginate and 0.5 mg/mL Matrigel and then printed onto the coated micropillars.

Growth media was then printed into the microwells on a microwell chip [103] using a microarray scanner.

The micropillar chip was then sandwiched with the microwell chip for 30 minutes and incubated for 24 hours with fresh growth media.

Next, various glycopolymers at 1250 μg/mL (polyacrylamide, N-glucosyl polymer, N-mannosyl polymer, N-lactosyl polymer, N-α2,3-sialolactosyl polymer, and N-α2,6-sialolactosyl polymer) and LPS at 10 μg/mL [701] were printed into the microwells.

The micropillar chip [101] was then sandwiched with the microwell plate containing glycopolymers and LPS [701] for 48 hours. The micropillar chip [101] was then rinsed with TBS [801] for 10 minutes, then incubated with ice-cold methanol and acetone (1:1 ratio) [802] for 10 minutes at room temperature. The micropillar chip [103] was then rinsed with TBS twice for 5 minutes and incubated with blocking buffer (SuperBlock) [803] for 1 hour at room temperature.

Next, primary antibodies (FITC-labeled rat anti-mouse CD40, CD1d, CD80, and I-A[d]) [804] were diluted in the blocking buffer [803] at 1:50 ratio to reach a final concentration of 0.01 mg/mL. The micropillar chip [101] was stained with the primary antibodies [804] at 4° C. for 6 hours. Then the micropillar chip [101] was stained with 1 μg/mL DAPI [805] for 30 minutes, then rinsed with TBS [801] twice for 10 minutes and coated with antifade reagent [806].

As shown in FIG. 14, the spots in the upper three images represent live immune cells expressing CD40 after exposure to polyacrylamide, and the spots in the lower three images represent the nucleus in the immune cell spheroids.

Figure 15A:
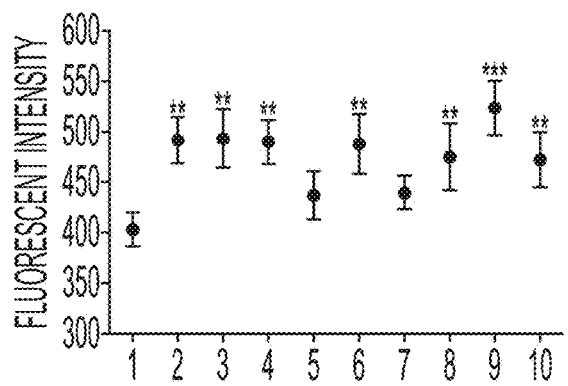
FIG. 15A is a graph showing results from Example 5.

FIGS. 15A-15D show the expression of cell surface biomarkers on RAW 264.7 cells after treatment with glycopolymers and LPS. FIG. 15A shows the expression of CD40, 15B shows the expression of CD80, 15C shows the expression of CD1d, and 15D shows the expression of Class II MHC. The numbers in FIGS. 15A-15D indicate as follows: 1 for growth medium control, 2 for LPS, 3 for polyacrylamide, 4 for N-glucosyl polymer, 5 for N-galactosyl polymer, 6 for N-mannosyl polymer, 7 for N-GlcNAc polymer, 8 for N-lactosyl polymer, 9 for N-α2,3-sialolactosyl polymer, and 10 for N-α2,6-sialolatosyl polymer. * for p<0.05,  for p<0.01, and * for p<0.001.

Figure 15B:
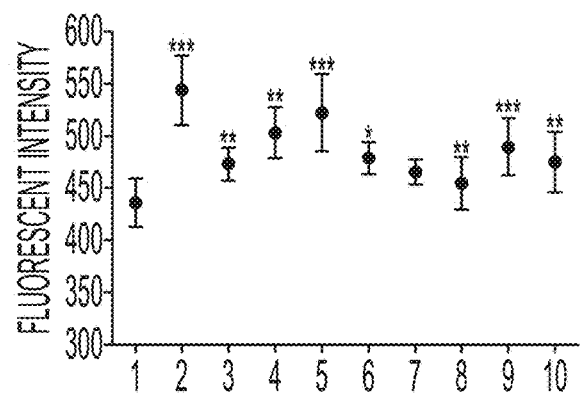
FIG. 15B is a graph showing results from Example 5.
Figure 15C:
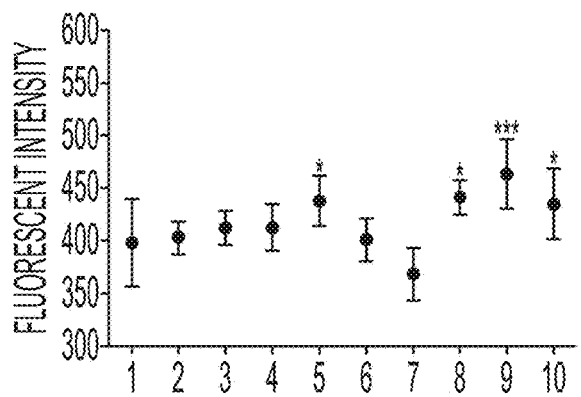
FIG. 15C is a graph showing results from Example 5.
Figure 15D:
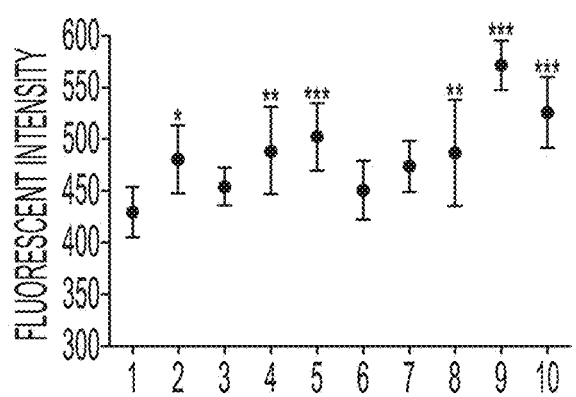
FIG. 15D is a graph showing results from Example 5.

In summary, LPS, polyacrylamide, N-glucosyl polymer, N-mannosyl polymer, N-lactosyl polymer, N-α2,3-sialolactosyl polymer, and N-α2,6-sialolactosyl polymer significantly enhanced the expression level of CD40 marker (FIG. 15A). LPS, N-glucosyl polymer, N-galactosyl polymer, N-mannosyl polymer, N-α2,3-sialolactosyl polymer, and N-α2,6-sialolactosyl polymer enhanced the expression level of CD80 marker (FIG. 15B). N-galactosyl polymer, N-lactosyl polymer, N-α2,3-sialolactosyl polymer, and N-α2,6-sialolactosyl polymer enhanced the expression level of CD1d marker (FIG. 15C). LPS, N-glucosyl polymer, N-galactosyl polymer, N-lactosyl polymer, N-α2,3-sialolactosyl polymer, and N-α2,6-sialolactosyl polymer significantly enhanced the expression level of class II MHC marker (FIG. 15D).

Measuring Soluble Factor Secretion

The general methods discussed above may be used to measure changes in soluble factors (e.g., cytokines, chemokines, growth factors, and interferons) secretion. This is generally done by printing immune cells [202] onto the micropillars [102] of a micropillar chip [101], exposing the immune cells to test compounds [701] that may modulate soluble factor secretion, then measuring or otherwise analyzing the secreted soluble factors [901].

Example 6

FIGS. 9 and 16A-D are discussed in this example. Example 6 demonstrates an exemplary embodiment of measuring cytokine secretion by immune cells using the micropillar/microwell platform disclosed herein.

The micropillars on a micropillar chip were coated with 0.01% PMA-OD. Then 16.6 mM $BaCl_2$/0.0033% PLL was printed on the micropillars [102] using a microarray spotter.

An immune-cell suspension was prepared using RAW 264.7 cells, 0.75% alginate and 0.5 mg/mL Matrigel and then printed onto the coated micropillars. 60 nL spots of the immune-cell suspension were printed onto a micropillar chip with dried PLL-$BaCl_2$ at a density of $3 \times 10^6$ cells/mL. After 2 minutes of alginate gelation and 24-hour incubation with a microwell chip containing 950 nL of cell growth media, the micropillar chip containing immune cells was sandwiched with a new microwell chip containing 950 nL of glycopolymers (polyacrylamide, N-glucosyl polymer, N-galactosyl polymer, N-mannosyl polymer, N-GlcNAc polymer, N-lactosyl polymer, N-α2,3 sialolactosyl polymer, and Nα2,6-sialolactosyl polymer) at 1250 μg/mL and LPS at 10 μg/mL, and incubated at 37° C. and 5% $CO_2$ for 24 hours.

Separately, immune cells were cultured in 96-well plates in growth media and 10 μg/mL LPS for 24 hours as negative and positive controls for 2D monolayer culture.

The cell supernatants for all conditions were collected from the microwell chip and the 96-well plate, centrifuged, and analyzed for 32-plex mouse cytokine array measurements.

Figure 16A:
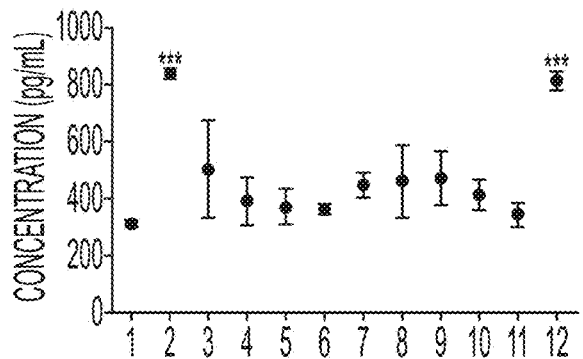
FIG. 16A is a graph showing results from Example 6.
Figure 16B:
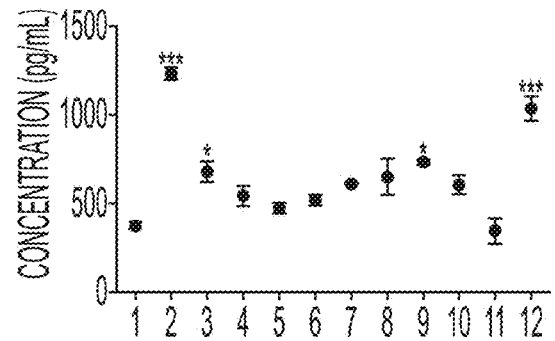
FIG. 16B is a graph showing results from Example 6.
Figure 16C:
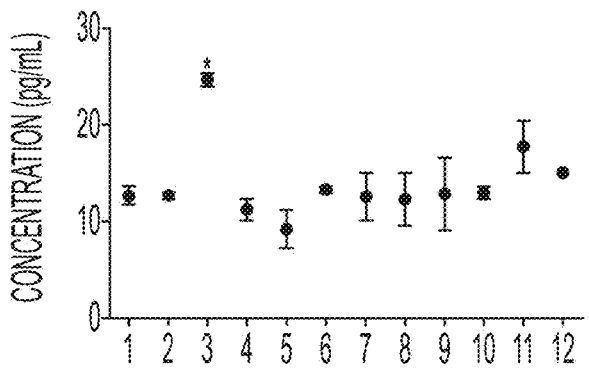
FIG. 16C is a graph showing results from Example 6.
Figure 16D:
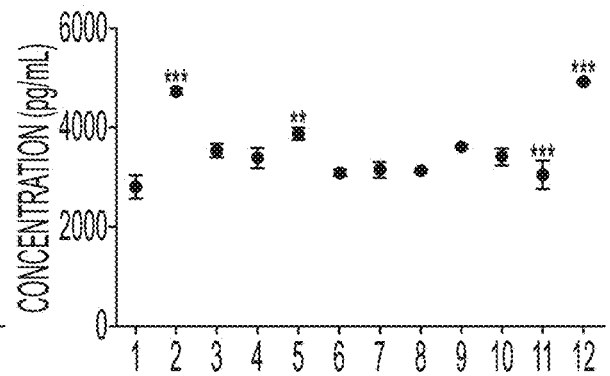
FIG. 16D is a graph showing results from Example 6.
Figure 16E:
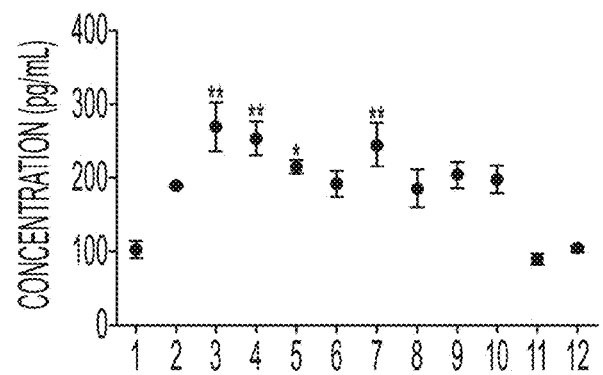
FIG. 16E is a graph showing results from Example 6.

FIGS. 16A-E show the expression of cytokines by RAW 264.7 cells after treatment with glycopolymers and LPS for 24 hours. FIG. 16A shows the expression of TNF-α, 16B shows the expression of IL-6, 16C shows the expression of IL-7, FIG. 16D shows the expression of IL-10, and FIG. 16D shows the expression of VEGF. The numbers indicate as follows: 1 for growth medium control, 2 for LPS, 3 for polyacrylamide, 4 for N-glucosyl polymer, 5 for N-galactosyl polymer, 6 for N-mannosyl polymer, 7 for N-GlcNAc polymer, 8 for N-lactosyl polymer, 9 for N-α2,3-sialolactosyl polymer, 10 for N-α2,6-sialolactosyl polymer (1-10 all from 384 micropillar chip), 11 for growth medium control, and 12 is for LPS, both 2D-cultured RAW 264.7 cells in 96-well plates. * for p<0.05,  for p<0.01, and * for p<0.001.

In summary, LPS significantly stimulated the cells for TNF-α, IL-6, and IL-10 production. Polyacrylamide stimulated the cells for IL-6, IL-7, and VEGF production, N-α2, 3-sialolactosyl polymer for IL-6 production, N-Galactosyl polymer for IL-10 and VEGF production, and N-glucosyl and N-GlcNAc polymers significantly stimulated the cells for VEGF production.

Although the present invention has been described in considerable detail with reference to certain preferred versions thereof, other versions are possible. Therefore, the spirit and scope of the appended claims should not be limited to the description of the preferred versions contained therein.

The multiplexed systemic immune cell assays described herein will find a wide range of basic research, clinical diagnosis, and biomedical and pharmaceutical screening applications. For example, these methods may be used for systematic evaluation of immune cell phenotypes for immunology research and application, systematic modulation of immune cells for immunology research and application, rapid functionality assessment of immune cell responses to synthetic ligands such as biomimetic glycoligands, multiplexed, high-throughput, and high-content imaging assays for immune cell functionality. In addition, these methods may have many commercial applications, such as immune cell phenotype and quality control, immune cell modulation for cancer treatment, screening of immunomodulation ligands, and immune cell targeting ligands.

The previously described versions of the present invention have many advantages, including rapid creation of 3D-cultured immune cells via novel microarray bioprinting technology; facilitation of rapid immune cell modulation on a micropillar/microwell chip platform with minimal manual intervention; miniaturization of multiplexed immune cell functionality assays (saving expensive resources, including cells, antibodies, growth factors, extracellular matrices, and reagents); high-throughput, systematic in situ study of immune cell responses to natural and synthetic ligands; high-throughput, high content imaging of miniaturized immune cell cultures for mechanistic studies; and detecting antibody-targeted molecules released upon cell activation in situ.

We claim:

1. A method comprising:
   a) dispensing immune cells onto a first micropillar;
   b) inserting the first micropillar into a microwell, in which the microwell contains at least one test compound, wherein the test compound is chosen to cause the immune cells to release a target molecule into the microwell, thereby creating a mixture;
   c) immobilizing antibodies onto a second micropillar, wherein the antibodies are chosen to target the target molecule;
   d) inserting the second micropillar having the immobilized antibodies into the microwell after step b), and allowing binding of the target molecule to the immobilized antibodies; and
   e) determining the amount of the target molecule in the mixture from the amount of target molecule bound to the immobilized antibodies.

2. The method of claim 1 wherein the second micropillar is first prepared by coating the surface with a reactive polymer.

3. The method of claim 2 wherein the reactive polymer consists of one or more polymers selected from the group containing poly(maleic anhydride-alt-1-octadecene), poly (styrene-co-maleic anhydride), poly-L-lysine, or combinations thereof.

4. The method of claim 1 wherein at least one ligand is attached to the second micropillar and the antibodies are attached to the at least one ligand.

5. The method of claim 4 wherein the at least one ligand is attached by dispensing the at least one ligand onto the second micropillar using a microarray spotter.

6. The method of claim 4 wherein the at least one ligand includes sulfo-NHS-biotin.

7. The method of claim 4 wherein the at least one ligand includes streptavidin.

8. The method of claim 4 wherein the at least one ligand includes carboxyphenyl boronic acid.

9. The method of claim 1 wherein the target molecule is an antigen or cytokine.

10. The method of claim 1 wherein the microwell contains a second test compound chosen to induce surface marker expression in the immune cells.

11. The method of claim 10 wherein following inserting the first micropillar into the microwell, the immune cells on the first micropillar are imaged to detect surface marker expression.

* * * * *